US012064145B2

(12) United States Patent
Keyer et al.

(10) Patent No.: US 12,064,145 B2
(45) Date of Patent: Aug. 20, 2024

(54) REVISION CONNECTOR FOR SPINAL CONSTRUCTS

(71) Applicant: DePuy Synthes Products, Inc., Raynham, MA (US)

(72) Inventors: Thomas Keyer, West Chester, PA (US); Eric McDivitt, Schwenksville, PA (US); Joseph Capozzoli, Mount Laurel, NJ (US); Christoph Meyer, Houston, TX (US); Nicholas Theodore, Ruxton, MD (US); Charles Kuntz, Cincinnati, OH (US)

(73) Assignee: DePuy Synthes Products, Inc., Raynham, MA (US)

( * ) Notice: Subject to any disclaimer, the term of this patent is extended or adjusted under 35 U.S.C. 154(b) by 646 days.

(21) Appl. No.: 17/242,361

(22) Filed: Apr. 28, 2021

(65) Prior Publication Data
US 2021/0251663 A1    Aug. 19, 2021

Related U.S. Application Data

(63) Continuation of application No. 16/140,680, filed on Sep. 25, 2018, now Pat. No. 11,020,152, which is a (Continued)

(51) Int. Cl.
*A61B 17/88* (2006.01)
*A61B 17/70* (2006.01)

(52) U.S. Cl.
CPC .................. *A61B 17/705* (2013.01)

(58) Field of Classification Search
CPC .............. A61B 17/7049; A61B 17/705; A61B 17/7052; A61B 17/7001; A61B 17/7032; A61B 17/7043
(Continued)

(56) References Cited

U.S. PATENT DOCUMENTS 405,546 A    6/1889    Frist
513,630 A    1/1894    Beard
(Continued)

FOREIGN PATENT DOCUMENTS

CA    2289629 A1    11/1998
CN    1997321 A     7/2007
(Continued)

OTHER PUBLICATIONS

Aebi et al., "AO ASIF Principles in Spine Surgery", Springer, 1998, 186-190.
(Continued)

*Primary Examiner* — Eduardo C Robert
*Assistant Examiner* — David C Comstock
(74) *Attorney, Agent, or Firm* — BakerHostetler

(57) ABSTRACT

A revision connector that is configured to couple a new spine fixation rod to a previously implanted spine fixation rod that is secured to a plurality of vertebrae. The previously implanted spine fixation rod may be received in a first rod receiving channel of the revision connector. The revision connector may include a linkage that is received in a second rod receiving channel of another revision connector. For example, the another revision connector may couple to the new spine fixation rod such that the revision connector is coupled to the new fixation rod. A bone anchor may not directly connect either of the revision connector or the another revision connector to underlying vertebra. Also, the new spine fixation rod can be implanted and secured to vertebra that are caudal and/or cranial with respect to the previously secured vertebrae.

20 Claims, 21 Drawing Sheets

Related U.S. Application Data continuation of application No. 12/760,816, filed on Apr. 15, 2010, now Pat. No. 10,105,163.

(60) Provisional application No. 61/169,336, filed on Apr. 15, 2009.

(58) Field of Classification Search
USPC ....... 606/259, 260, 264, 265, 267, 270, 272, 606/278, 279
See application file for complete search history.

(56) References Cited

U.S. PATENT DOCUMENTS

| | | |
|---|---|---|
| 527,678 A | 10/1894 | Francis |
| 802,896 A | 10/1905 | Webb |
| 2,005,348 A | 6/1935 | Michell |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox et al. |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Vignaud et al. |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Miller et al. |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann et al. |
| 5,449,361 A | 9/1995 | Preissman |
| 5,466,237 A | 11/1995 | Byrd et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlaepfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman |
| 5,549,608 A | 8/1996 | Errico et al. |
| 5,549,677 A | 8/1996 | Duerr et al. |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,260 A | 7/1997 | Doherty |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A | 7/1997 | Errico et al. |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi et al. |
| 5,902,305 A | 5/1999 | Beger et al. |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Schlaepfer |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael et al. |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers et al. |
| 6,224,598 B1 | 5/2001 | Jackson |
| 6,248,105 B1 | 6/2001 | Schlaepfer et al. |
| 6,261,287 B1 | 7/2001 | Metz-Stavenhagen |
| 6,273,914 B1 | 8/2001 | Papas |
| 6,280,442 B1 | 8/2001 | Barker et al. |
| 6,296,642 B1 | 10/2001 | Morrison et al. |
| 6,325,802 B1 | 12/2001 | Frigg |
| 6,355,040 B1 | 3/2002 | Richelsoph et al. |
| 6,361,535 B2 | 3/2002 | Jackson |
| RE37,665 E | 4/2002 | Ralph et al. |
| 6,368,320 B1 * | 4/2002 | Le Couedic ....... A61B 17/7049 606/246 |

(56) References Cited

U.S. PATENT DOCUMENTS

| | | |
|---|---|---|
| 6,368,321 B1 | 4/2002 | Jackson |
| 6,402,752 B2 | 6/2002 | Schaeffler-Wachter et al. |
| 6,440,132 B1 | 8/2002 | Jackson |
| 6,443,953 B1 | 9/2002 | Perra et al. |
| 6,443,955 B1 | 9/2002 | Ahrend et al. |
| 6,451,021 B1 | 9/2002 | Ralph et al. |
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Cooper et al. |
| 6,641,586 B2 | 11/2003 | Varieur |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,866,664 B2 | 3/2005 | Schaer et al. |
| 6,869,433 B2 | 3/2005 | Glascott |
| 6,887,275 B2 | 5/2005 | Carchidi et al. |
| 6,918,911 B2 | 7/2005 | Biedermann et al. |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael et al. |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| 7,094,240 B2 | 8/2006 | Molz, IV et al. |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 | 11/2008 | Hawkes et al. |
| 7,452,360 B2 | 11/2008 | Trudeau et al. |
| 7,476,239 B2 | 1/2009 | Jackson |
| 7,547,319 B2 | 6/2009 | Segal et al. |
| 7,572,281 B2 | 8/2009 | Runco et al. |
| 7,591,839 B2 | 9/2009 | Biedermann et al. |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 | 8/2010 | Marino et al. |
| 7,785,352 B2 | 8/2010 | Snyder et al. |
| 7,785,354 B2 | 8/2010 | Biedermann et al. |
| 7,799,054 B2 | 9/2010 | Kwak et al. |
| 7,803,174 B2 | 9/2010 | Denis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 | 8/2011 | Justis |
| 8,029,513 B2 | 10/2011 | Konno et al. |
| 8,029,544 B2 | 10/2011 | Hestad et al. |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,162,946 B2 | 4/2012 | Baccelli et al. |
| 8,162,986 B2 | 4/2012 | Zehnder |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 | 11/2012 | Zucherman et al. |
| 8,323,318 B2 | 12/2012 | Baccelli et al. |
| 8,444,681 B2 | 5/2013 | Jackson et al. |
| 8,469,960 B2 | 6/2013 | Hutton et al. |
| 8,469,966 B2 | 6/2013 | Allen et al. |
| 8,556,938 B2 | 10/2013 | Jackson et al. |
| 8,628,558 B2 | 1/2014 | Harvey et al. |
| 8,632,572 B2 | 1/2014 | Darst et al. |
| 8,663,298 B2 | 3/2014 | Keyer et al. |
| 8,758,411 B1 | 6/2014 | Rayon et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,470 B2 | 12/2014 | Mirza et al. |
| 8,911,478 B2 | 12/2014 | Jackson et al. |
| 8,911,479 B2 | 12/2014 | Jackson et al. |
| 8,926,672 B2 | 1/2015 | Jackson et al. |
| 8,979,904 B2 | 3/2015 | Jackson et al. |
| 8,998,959 B2 | 4/2015 | Jackson et al. |
| 8,998,961 B1 | 4/2015 | Ziemek et al. |
| 9,039,708 B2 | 5/2015 | Larroque-Lahitette |
| 9,168,069 B2 | 10/2015 | Jackson et al. |
| 9,216,041 B2 | 12/2015 | Jackson et al. |
| 9,320,546 B2 | 4/2016 | Keyer et al. |
| 9,326,796 B2 | 5/2016 | Harvey et al. |
| 9,393,047 B2 | 7/2016 | Jackson et al. |
| 9,439,681 B2 | 9/2016 | Keyer et al. |
| 9,451,993 B2 | 9/2016 | Jackson et al. |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,636,146 B2 | 5/2017 | Jackson et al. |
| 9,717,533 B2 | 8/2017 | Jackson et al. |
| 9,717,534 B2 | 8/2017 | Jackson et al. |
| 10,105,163 B2 | 10/2018 | Keyer et al. |

(56) References Cited

U.S. PATENT DOCUMENTS

| | | |
|---|---|---|
| 10,136,923 B2 | 11/2018 | Keyer et al. |
| 10,154,859 B2 | 12/2018 | Keyer et al. |
| 10,405,892 B2 | 9/2019 | Harvey et al. |
| 10,595,908 B2 | 3/2020 | Strausbaugh et al. |
| 11,357,550 B2 | 6/2022 | Keyer et al. |
| 2001/0047173 A1 | 11/2001 | Schlapfer et al. |
| 2002/0045899 A1 | 4/2002 | Errico et al. |
| 2002/0068940 A1 | 6/2002 | Gaines |
| 2002/0069537 A1 | 6/2002 | Wenzler |
| 2002/0072753 A1 | 6/2002 | Cohen |
| 2002/0103487 A1 | 8/2002 | Errico et al. |
| 2002/0117321 A1 | 8/2002 | Beebe et al. |
| 2002/0120272 A1 | 8/2002 | Yuan et al. |
| 2002/0133154 A1 | 9/2002 | Saint Martin |
| 2002/0138077 A1 | 9/2002 | Ferree |
| 2002/0143341 A1 | 10/2002 | Biedermann et al. |
| 2002/0151900 A1 | 10/2002 | Glascott |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0125742 A1 | 7/2003 | Yuan et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0176861 A1 | 9/2003 | Reed |
| 2004/0006342 A1 | 1/2004 | Altarac et al. |
| 2004/0024464 A1 | 2/2004 | Errico et al. |
| 2004/0039384 A1 | 2/2004 | Boehm et al. |
| 2004/0111088 A1 | 6/2004 | Picetti et al. |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0157186 A1 | 8/2004 | Abels et al. |
| 2004/0162558 A1 | 8/2004 | Hegde et al. |
| 2004/0172022 A1 | 9/2004 | Landry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0199169 A1 | 10/2004 | Koons et al. |
| 2004/0225292 A1 | 11/2004 | Sasso et al. |
| 2004/0230192 A1 | 11/2004 | Graf |
| 2004/0236330 A1 | 11/2004 | Purcell et al. |
| 2004/0249378 A1 | 12/2004 | Saint et al. |
| 2004/0249380 A1 | 12/2004 | Glascott |
| 2004/0267264 A1 | 12/2004 | Konieczynski et al. |
| 2005/0033298 A1 | 2/2005 | Hawkes et al. |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0080415 A1 | 4/2005 | Keyer et al. |
| 2005/0080420 A1 | 4/2005 | Farris et al. |
| 2005/0143737 A1 | 6/2005 | Pafford et al. |
| 2005/0154389 A1 | 7/2005 | Selover et al. |
| 2005/0154391 A1 | 7/2005 | Doherty et al. |
| 2005/0171537 A1 | 8/2005 | Mazel et al. |
| 2005/0171542 A1 | 8/2005 | Biedermann et al. |
| 2005/0177154 A1 | 8/2005 | Moumene et al. |
| 2005/0177166 A1 | 8/2005 | Timm et al. |
| 2005/0177179 A1 | 8/2005 | Baynham et al. |
| 2005/0187548 A1 | 8/2005 | Butler et al. |
| 2005/0192571 A1 | 9/2005 | Abdelgany |
| 2005/0203515 A1 | 9/2005 | Doherty et al. |
| 2005/0203516 A1 | 9/2005 | Biedermann et al. |
| 2005/0209592 A1 | 9/2005 | Schlapfer et al. |
| 2005/0216001 A1 | 9/2005 | David |
| 2005/0216003 A1 | 9/2005 | Biedermann et al. |
| 2005/0228378 A1 | 10/2005 | Kalfas et al. |
| 2005/0228385 A1 | 10/2005 | Iott et al. |
| 2005/0234421 A1 | 10/2005 | Mishima et al. |
| 2005/0234451 A1 | 10/2005 | Markworth |
| 2005/0261687 A1 | 11/2005 | Garamszegi et al. |
| 2005/0277928 A1 | 12/2005 | Boschert |
| 2005/0283157 A1 | 12/2005 | Coates et al. |
| 2005/0288671 A1 | 12/2005 | Yuan et al. |
| 2006/0004357 A1 | 1/2006 | Lee et al. |
| 2006/0025767 A1 | 2/2006 | Khalili |
| 2006/0025770 A1 | 2/2006 | Schlapfer et al. |
| 2006/0036252 A1 | 2/2006 | Baynham et al. |
| 2006/0052818 A1 | 3/2006 | Drake et al. |
| 2006/0064091 A1 | 3/2006 | Ludwig et al. |
| 2006/0079892 A1 | 4/2006 | Roychowdhury et al. |
| 2006/0084993 A1 | 4/2006 | Landry et al. |
| 2006/0084995 A1 | 4/2006 | Biedermann et al. |
| 2006/0084996 A1 | 4/2006 | Metz-Stavenhagen |
| 2006/0089634 A1 | 4/2006 | Anderson et al. |
| 2006/0089643 A1 | 4/2006 | Mujwid |
| 2006/0100622 A1 | 5/2006 | Jackson |
| 2006/0106383 A1 | 5/2006 | Biedermann et al. |
| 2006/0111779 A1 | 5/2006 | Petersen |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149233 A1 | 7/2006 | Richelsoph |
| 2006/0149241 A1 | 7/2006 | Richelsoph et al. |
| 2006/0149244 A1 | 7/2006 | Amrein et al. |
| 2006/0149265 A1 | 7/2006 | James et al. |
| 2006/0155277 A1 | 7/2006 | Metz-Stavenhagen |
| 2006/0173456 A1 | 8/2006 | Hawkes et al. |
| 2006/0200131 A1 | 9/2006 | Chao et al. |
| 2006/0212034 A1 | 9/2006 | Triplett et al. |
| 2006/0217717 A1 | 9/2006 | Whipple |
| 2006/0229611 A1 | 10/2006 | Avery et al. |
| 2006/0235385 A1 | 10/2006 | Whipple |
| 2006/0235393 A1 | 10/2006 | Bono et al. |
| 2006/0241594 A1 | 10/2006 | McCarthy et al. |
| 2006/0241599 A1 | 10/2006 | Konieczynski et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2006/0271047 A1 | 11/2006 | Jackson |
| 2006/0282080 A1 | 12/2006 | Todd et al. |
| 2006/0293659 A1 | 12/2006 | Alvarez |
| 2006/0293664 A1 | 12/2006 | Schumacher |
| 2007/0016200 A1 | 1/2007 | Jackson |
| 2007/0043365 A1 | 2/2007 | Ritland |
| 2007/0049932 A1 | 3/2007 | Richelsoph et al. |
| 2007/0055240 A1 | 3/2007 | Matthis et al. |
| 2007/0088357 A1 | 4/2007 | Johnson et al. |
| 2007/0090238 A1 | 4/2007 | Justis |
| 2007/0118118 A1 | 5/2007 | Kwak et al. |
| 2007/0118121 A1 | 5/2007 | Purcell et al. |
| 2007/0118123 A1 | 5/2007 | Strausbaugh et al. |
| 2007/0123860 A1 | 5/2007 | Francis et al. |
| 2007/0123870 A1 | 5/2007 | Jeon et al. |
| 2007/0135817 A1 | 6/2007 | Ensign |
| 2007/0161987 A1 | 7/2007 | Capote et al. |
| 2007/0161994 A1 | 7/2007 | Lowery et al. |
| 2007/0167946 A1 | 7/2007 | Triplett et al. |
| 2007/0167949 A1 | 7/2007 | Altarac et al. |
| 2007/0179501 A1 | 8/2007 | Firkins |
| 2007/0191844 A1 | 8/2007 | Carls et al. |
| 2007/0198014 A1 | 8/2007 | Graf et al. |
| 2007/0225711 A1 | 9/2007 | Ensign |
| 2007/0233087 A1 | 10/2007 | Schlapfer |
| 2007/0233091 A1 | 10/2007 | Naifeh et al. |
| 2007/0246614 A1 | 10/2007 | Allmann et al. |
| 2007/0250061 A1 | 10/2007 | Chin et al. |
| 2007/0250064 A1 | 10/2007 | Darois et al. |
| 2007/0270805 A1 | 11/2007 | Miller et al. |
| 2007/0270817 A1 | 11/2007 | Rezach |
| 2007/0270820 A1 | 11/2007 | Dickinson et al. |
| 2007/0270880 A1 | 11/2007 | Lindemann et al. |
| 2007/0282339 A1 | 12/2007 | Schwab |
| 2007/0288004 A1 | 12/2007 | Alvarez |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0058805 A1 | 3/2008 | Stuart |
| 2008/0058812 A1 | 3/2008 | Zehnder |
| 2008/0086126 A1 | 4/2008 | Miller |
| 2008/0103502 A1 | 5/2008 | Capote et al. |
| 2008/0140075 A1 | 6/2008 | Ensign et al. |

(56) References Cited

U.S. PATENT DOCUMENTS

| | | |
|---|---|---|
| 2008/0140135 A1 | 6/2008 | Konieczynski et al. |
| 2008/0154277 A1 | 6/2008 | Machalk et al. |
| 2008/0154308 A1 | 6/2008 | Sherman et al. |
| 2008/0177260 A1 | 7/2008 | McKinley et al. |
| 2008/0177323 A1 | 7/2008 | Null et al. |
| 2008/0188260 A1 | 8/2008 | Xiao et al. |
| 2008/0208257 A1 | 8/2008 | Matthys |
| 2008/0215095 A1 | 9/2008 | Biedermann et al. |
| 2008/0234743 A1 | 9/2008 | Marik |
| 2008/0243185 A1 | 10/2008 | Felix et al. |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1 | 11/2008 | Capote et al. |
| 2008/0294202 A1 | 11/2008 | Peterson et al. |
| 2008/0306553 A1 | 12/2008 | Zucherman et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets et al. |
| 2009/0149887 A1 | 6/2009 | Schlaepfer et al. |
| 2009/0163955 A1 | 6/2009 | Moumene et al. |
| 2009/0177231 A1 | 7/2009 | Kiester |
| 2009/0187217 A1 | 7/2009 | Weiman et al. |
| 2009/0198279 A1* | 8/2009 | Zhang ............... A61B 17/7023 606/301 |
| 2009/0198280 A1 | 8/2009 | Spratt et al. |
| 2009/0222042 A1* | 9/2009 | Firkins ............... A61B 17/701 606/261 |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0249843 A1 | 9/2010 | Wegrzyn, III |
| 2010/0276051 A1 | 11/2010 | Kanehira |
| 2010/0292736 A1 | 11/2010 | Schwab |
| 2010/0298890 A1 | 11/2010 | Marino |
| 2010/0298891 A1 | 11/2010 | Jackson |
| 2010/0305621 A1 | 12/2010 | Wang et al. |
| 2010/0313428 A1 | 12/2010 | Mocanu |
| 2010/0318131 A1 | 12/2010 | James et al. |
| 2010/0324599 A1 | 12/2010 | Montello et al. |
| 2011/0087289 A1 | 4/2011 | Pham et al. |
| 2011/0106166 A1 | 5/2011 | Keyer et al. |
| 2011/0118791 A1 | 5/2011 | Nunley et al. |
| 2011/0172717 A1* | 7/2011 | Miller ............... A61B 17/7014 606/279 |
| 2011/0213424 A1 | 9/2011 | Biedermann et al. |
| 2011/0230917 A1 | 9/2011 | Carson et al. |
| 2011/0270325 A1 | 11/2011 | Keyer et al. |
| 2011/0276051 A1 | 11/2011 | Blakemore et al. |
| 2012/0010629 A1 | 1/2012 | Mire et al. |
| 2012/0089194 A1 | 4/2012 | Strausbaugh et al. |
| 2012/0101533 A1 | 4/2012 | Purcell et al. |
| 2012/0109200 A1 | 5/2012 | Cahill et al. |
| 2012/0265249 A1 | 10/2012 | Fielding et al. |
| 2013/0012955 A1 | 1/2013 | Lin |
| 2013/0012995 A1 | 1/2013 | Butterfield et al. |
| 2013/0018421 A1 | 1/2013 | George et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |
| 2018/0036041 A1 | 2/2018 | Pham et al. |

FOREIGN PATENT DOCUMENTS

| | | |
|---|---|---|
| CN | 101249017 A | 8/2008 |
| CN | 102368967 A | 3/2012 |
| CN | 102458279 A | 5/2012 |
| DE | 9314297 U1 | 4/1994 |
| DE | 4329220 A1 | 3/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 B1 | 9/1994 |
| EP | 0674880 A1 | 10/1995 |
| EP | 0828459 A1 | 3/1998 |
| EP | 0837656 A1 | 4/1998 |
| EP | 0612507 B1 | 12/1998 |
| EP | 0683644 B1 | 6/2000 |
| EP | 1198205 A1 | 4/2002 |
| EP | 1210914 A1 | 6/2002 |
| EP | 0807420 B1 | 7/2002 |
| EP | 1248573 A1 | 10/2002 |
| EP | 1269929 A1 | 1/2003 |
| EP | 1316295 A2 | 6/2003 |
| EP | 1323391 A2 | 7/2003 |
| EP | 1637085 A2 | 3/2006 |
| EP | 1313403 B1 | 10/2006 |
| EP | 1741396 A1 | 1/2007 |
| EP | 1815812 A1 | 8/2007 |
| EP | 1665994 B1 | 6/2008 |
| EP | 1928358 A2 | 6/2008 |
| EP | 1961392 A1 | 8/2008 |
| EP | 2052690 A1 | 4/2009 |
| EP | 1294297 B1 | 8/2010 |
| ES | 2330132 T3 | 12/2009 |
| GB | 0820252 | 9/1959 |
| GB | 2414674 B | 8/2009 |
| GB | 2465156 A | 5/2010 |
| JP | 06-154258 | 6/1994 |
| JP | 08-112291 A | 5/1996 |
| JP | 2005-510286 | 4/2005 |
| JP | 2006-508748 A | 3/2006 |
| JP | 2006-154258 | 6/2006 |
| JP | 2006-525102 A | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 10-0896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | 97/02786 A1 | 1/1997 |
| WO | 98/08454 | 3/1998 |
| WO | 98/52482 A1 | 11/1998 |
| WO | 2000/015125 A1 | 3/2000 |
| WO | 00/21455 A1 | 4/2000 |
| WO | 01/06940 A1 | 2/2001 |
| WO | 01/52758 A1 | 7/2001 |
| WO | 02/00124 A1 | 1/2002 |
| WO | 02/17803 A2 | 3/2002 |
| WO | 02/76314 A1 | 10/2002 |
| WO | 2003/045261 A1 | 6/2003 |
| WO | 2004/052218 A1 | 6/2004 |
| WO | 2004/089245 A2 | 10/2004 |
| WO | 2004/098425 A2 | 11/2004 |
| WO | 2005/016161 A1 | 2/2005 |
| WO | 2006/088452 A2 | 8/2006 |
| WO | 2006/114437 A1 | 11/2006 |
| WO | 2006/116437 A2 | 11/2006 |
| WO | 2006/135555 A2 | 12/2006 |
| WO | 2007/038350 A1 | 4/2007 |
| WO | 2007/040824 A2 | 4/2007 |
| WO | 2007/045892 A1 | 4/2007 |
| WO | 2007/047711 A2 | 4/2007 |
| WO | 2007/127632 A2 | 11/2007 |
| WO | 2007/146032 A2 | 12/2007 |
| WO | 2008/027940 A1 | 3/2008 |
| WO | 2008/048953 A2 | 4/2008 |

(56) References Cited

FOREIGN PATENT DOCUMENTS

| WO | 2008/069420 A1 | 6/2008 |
| WO | 2008/089096 A2 | 7/2008 |
| WO | 2008/146185 A1 | 12/2008 |
| WO | 2008/147663 A1 | 12/2008 |
| WO | 2009/001978 A1 | 12/2008 |
| WO | 2009/015100 A2 | 1/2009 |
| WO | 2010/030906 A1 | 3/2010 |
| WO | 2010/028287 A3 | 6/2010 |
| WO | 2010/120989 A1 | 10/2010 |
| WO | 2010/148231 A1 | 12/2010 |
| WO | 2012/154772 A2 | 11/2012 |

OTHER PUBLICATIONS

International Patent Application No. PCT/US2006/037120: International Search Report dated Jul. 11, 2007, 4 pages.
International Patent Application No. PCT/US2006/047986: International Search Report dated May 2, 2007, 2 pages.
International Patent Application No. PCT/US2010/031178: International Search Report dated Jun. 22, 2010, 8 pages.
International Patent Application No. PCT/US2008/070670: International Search Report dated Feb. 17, 2009, 3 pages.
International Patent Application No. PCT/US2010/031178: Notification of Transmittal of The International Preliminary Report on patentability, 21 pages., Nov. 22, 2016.
International Patent Application No. PCT/US2010/039037: International Preliminary Report on Patentability dated Jul. 11, 2011.
International Patent Application No. PCT/US2010/039037: International Search Report Dated Jan. 9, 2010, 5 pages.
U.S. Appl. No. 16/140,680, filed Sep. 25, 2018.
U.S. Appl. No. 12/760,816, filed Apr. 15, 2010.

\* cited by examiner

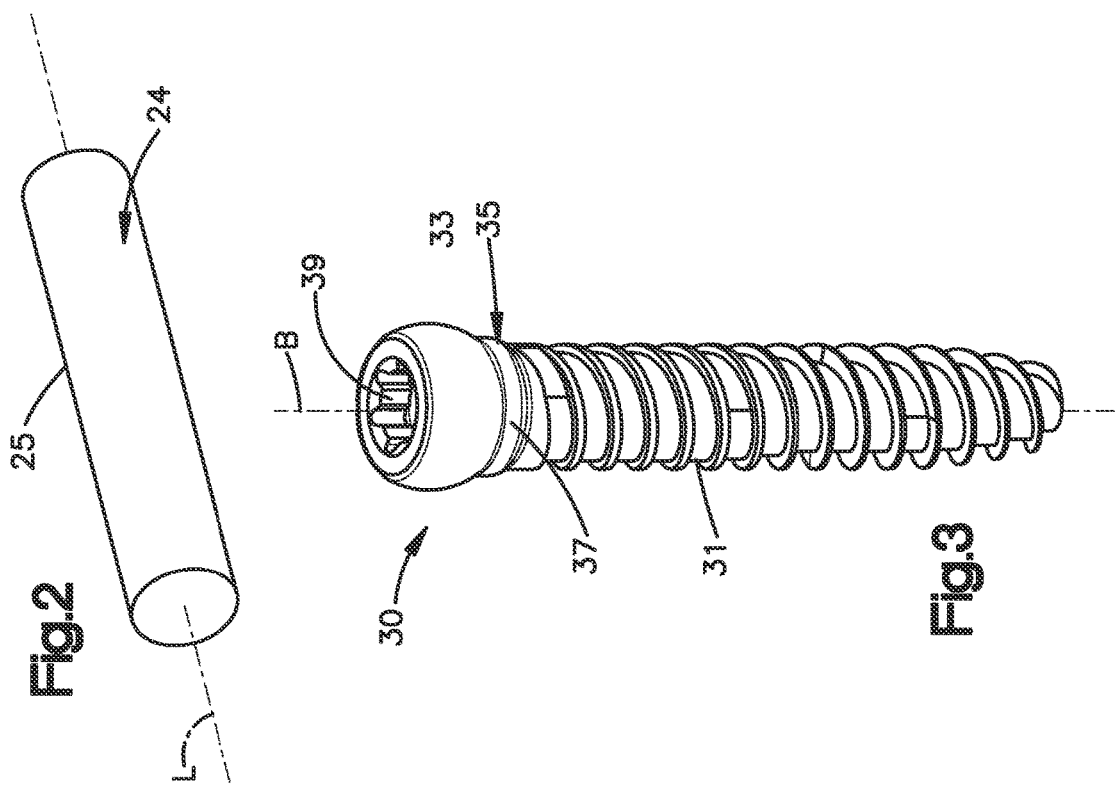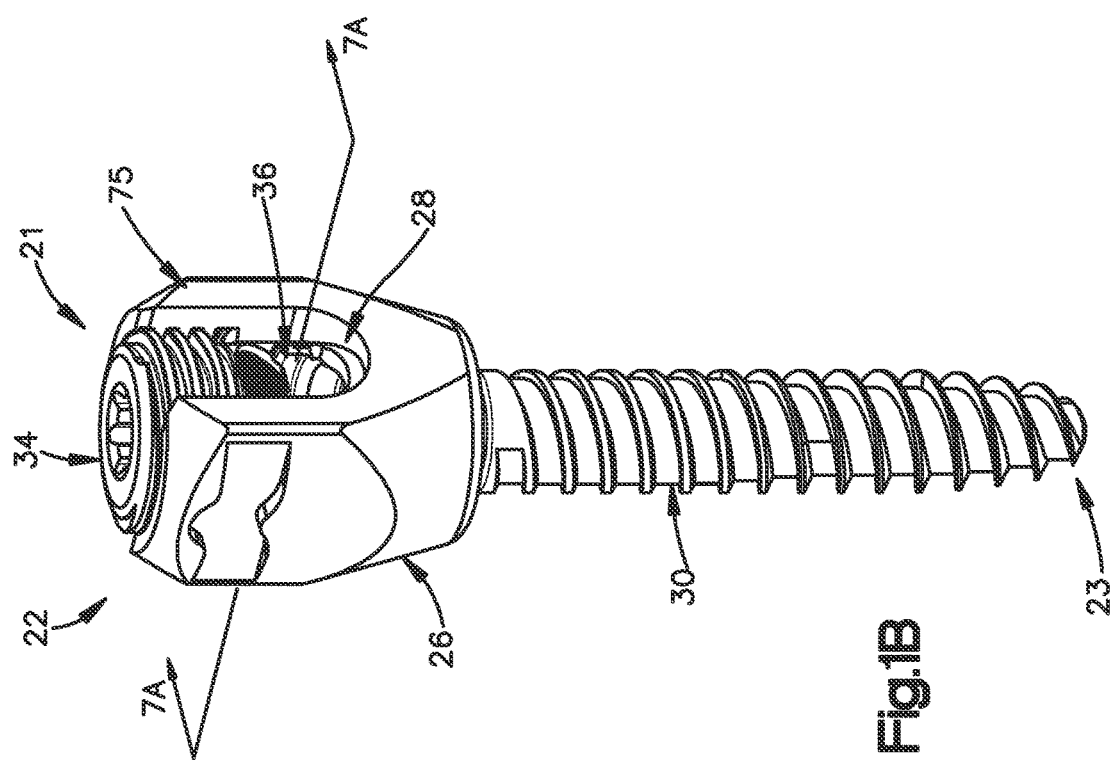

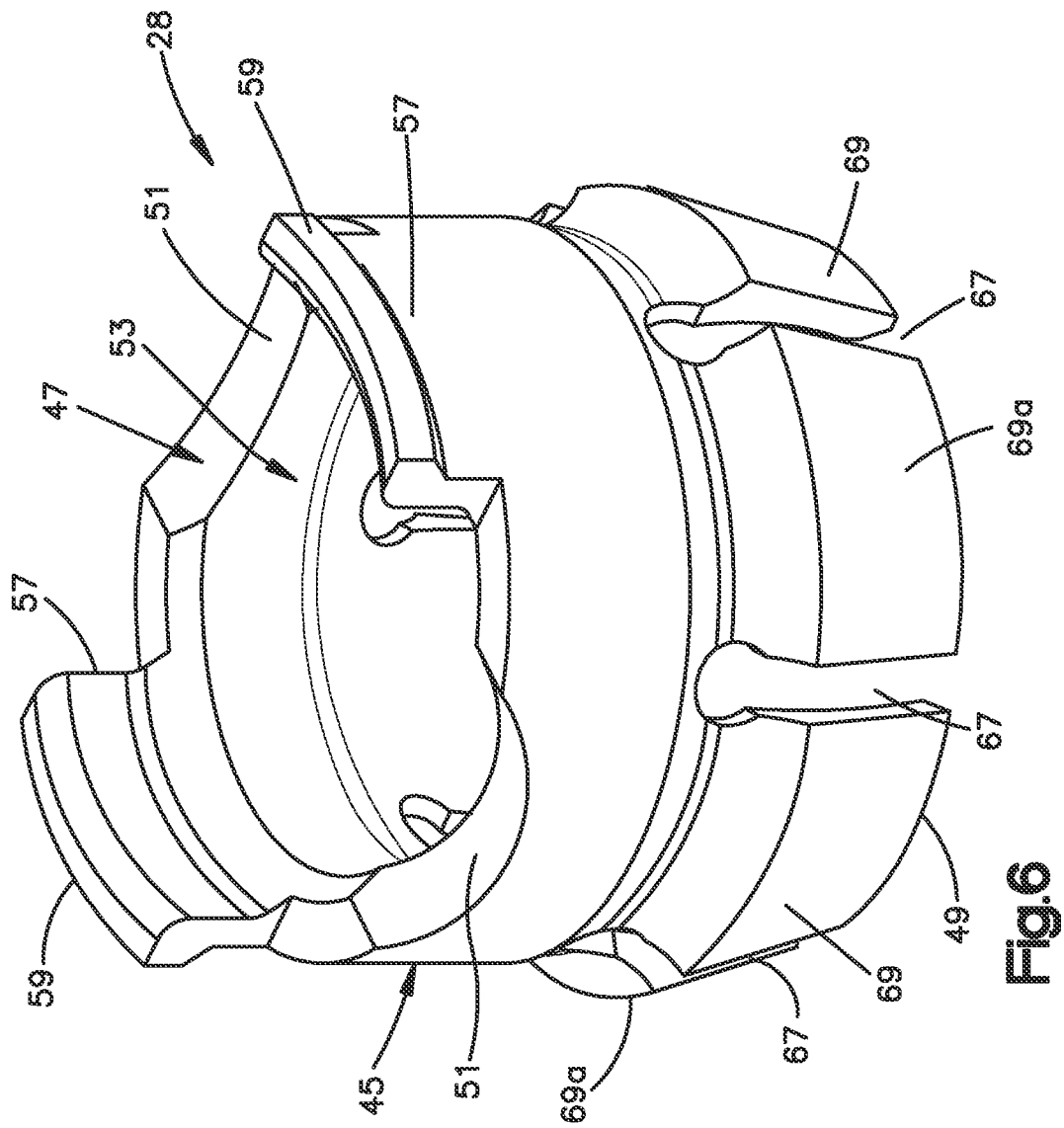

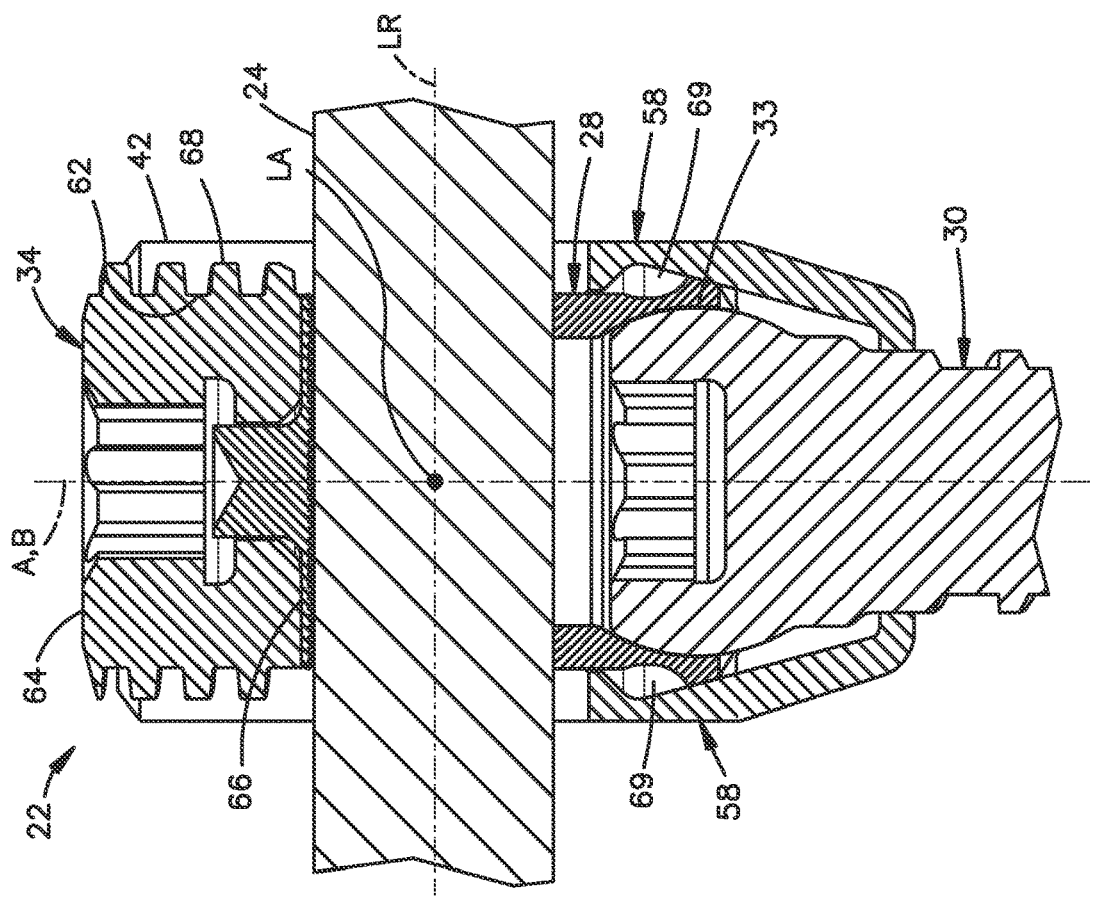
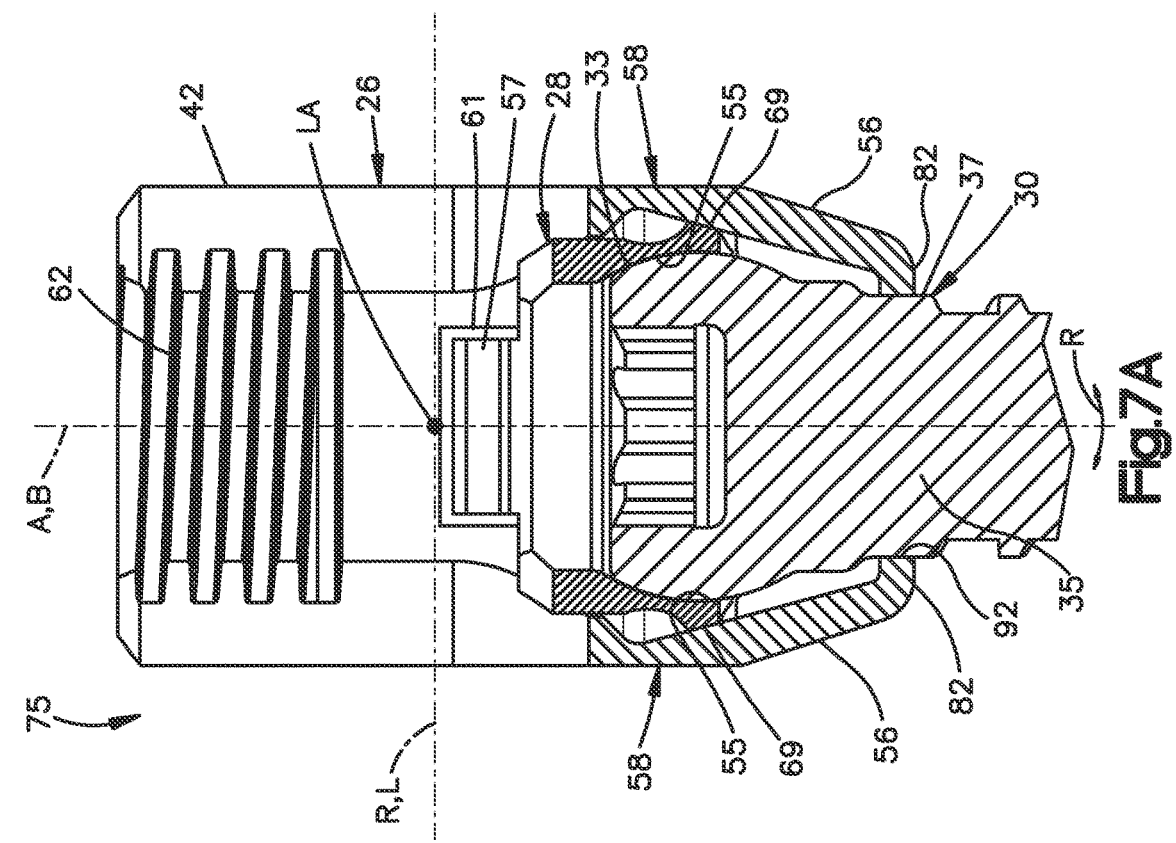

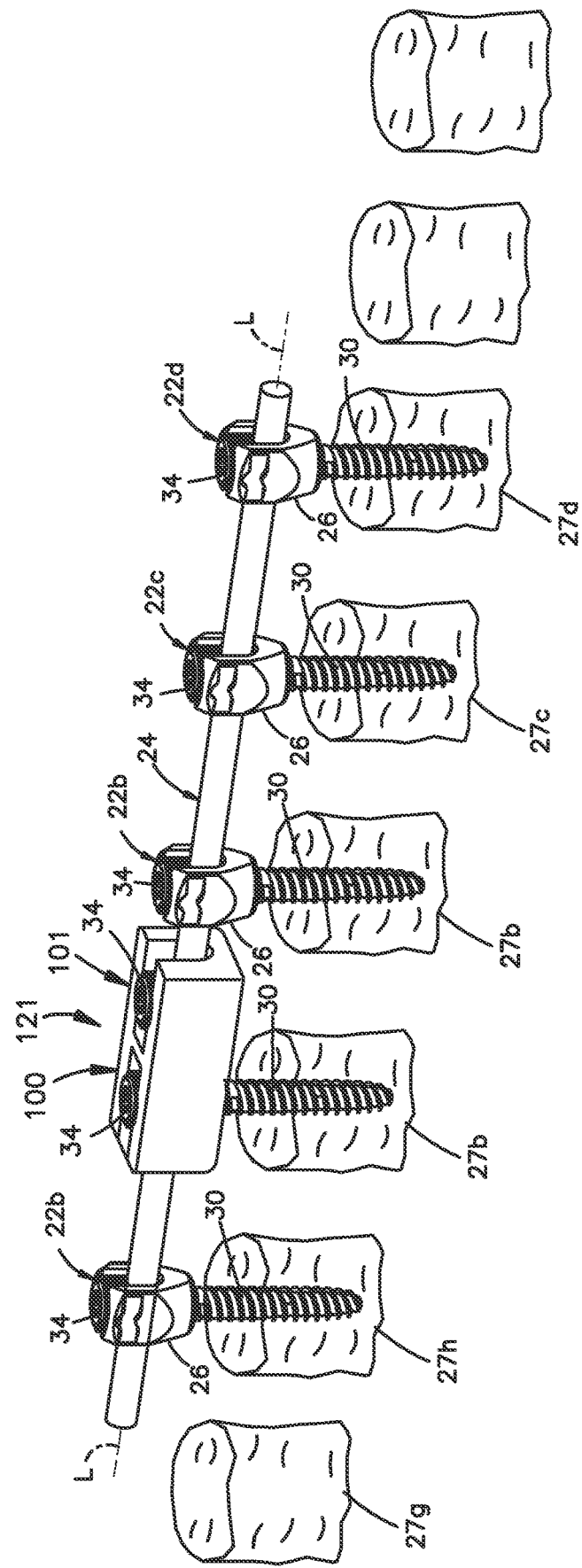

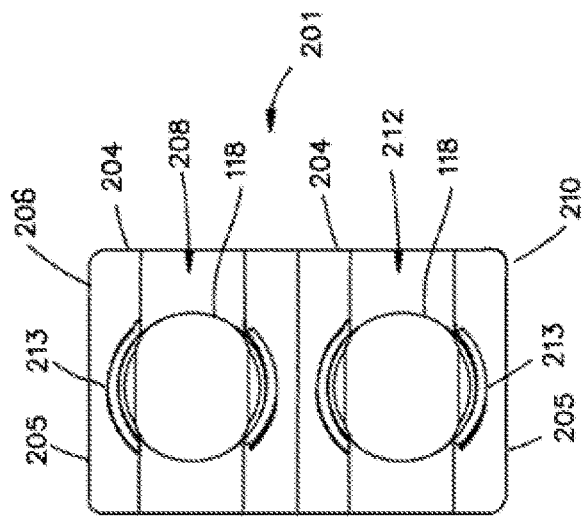
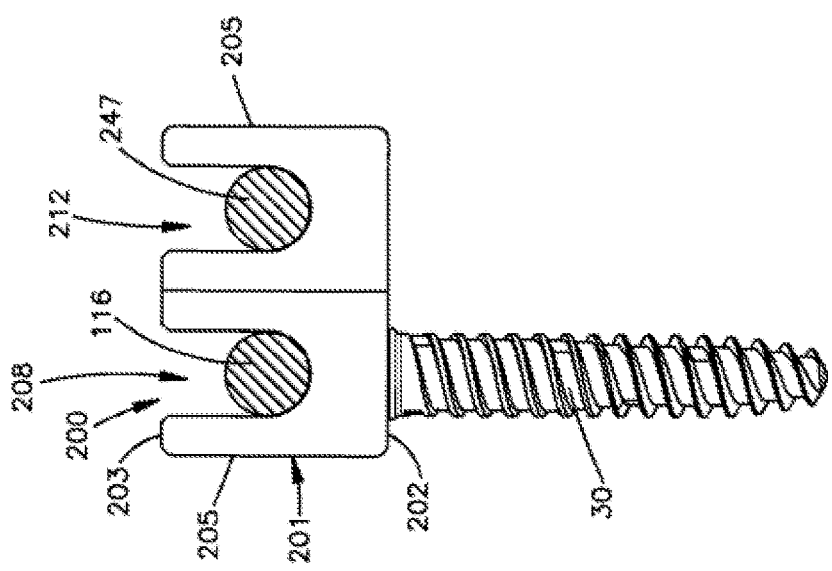
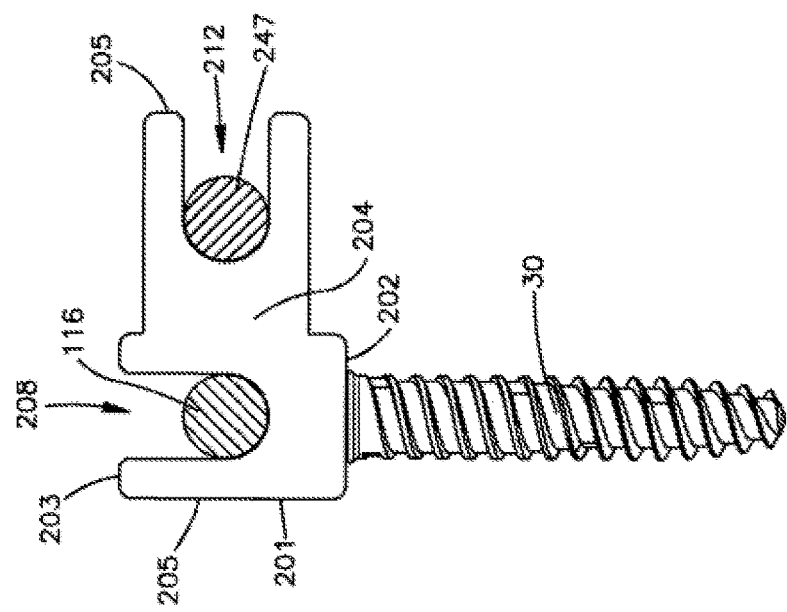

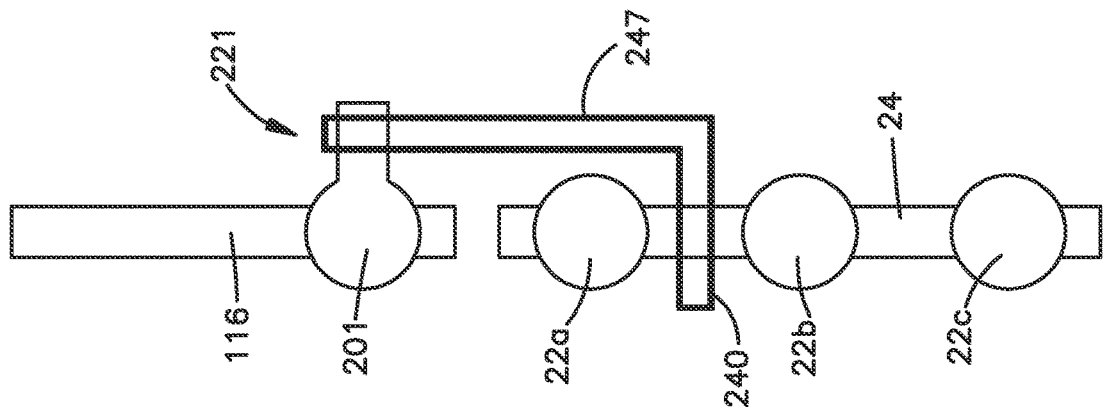
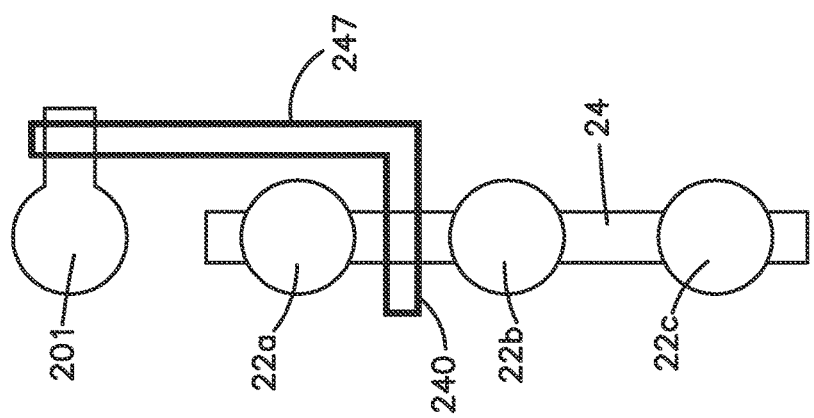
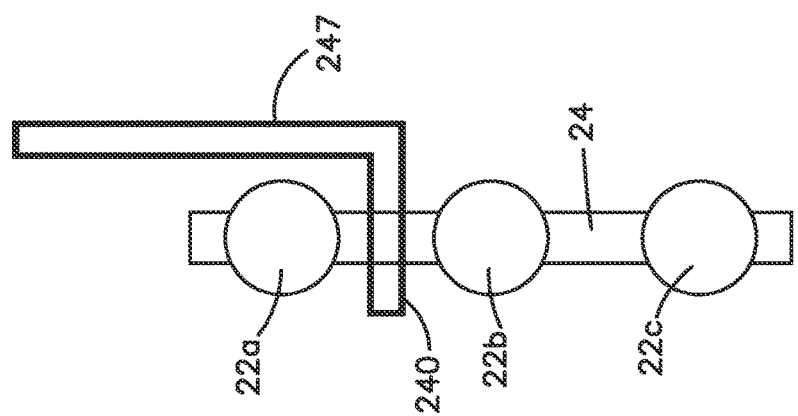
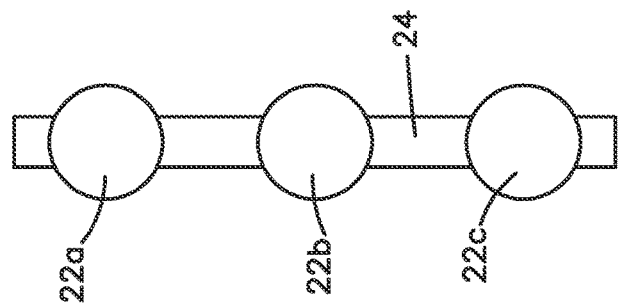

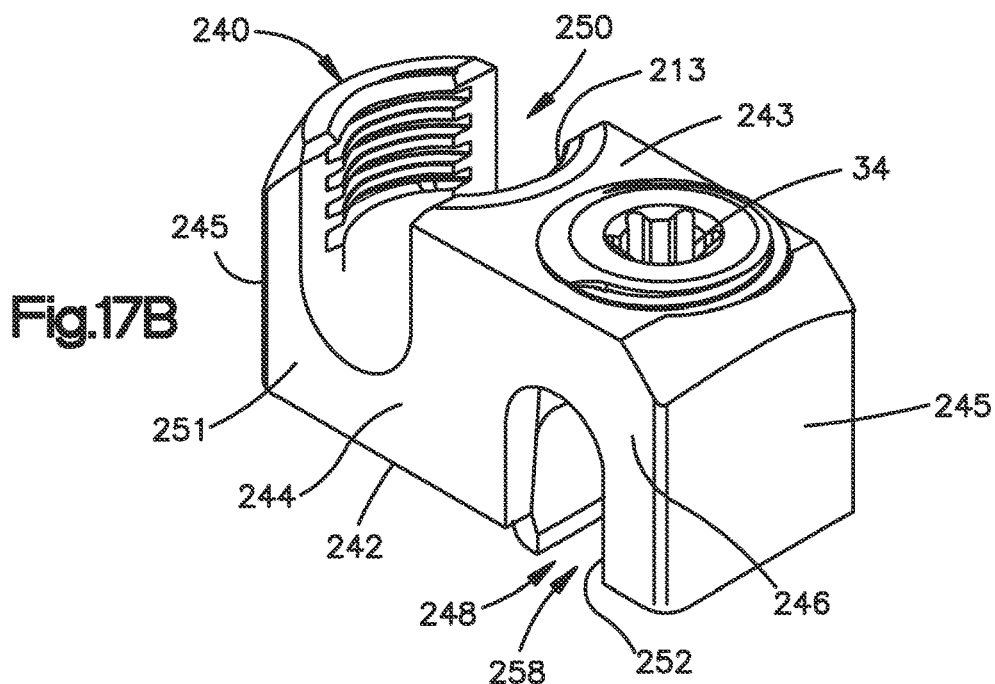
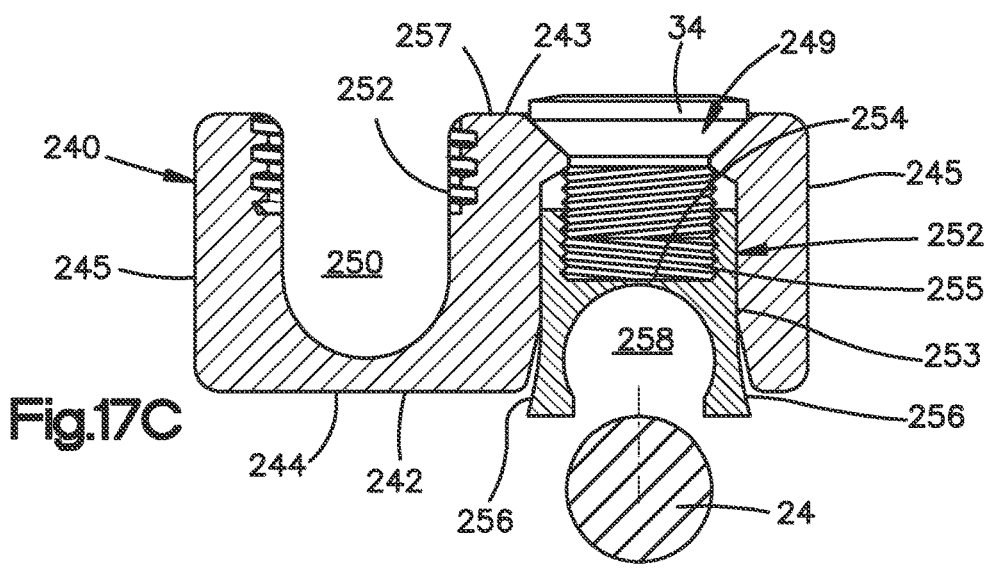
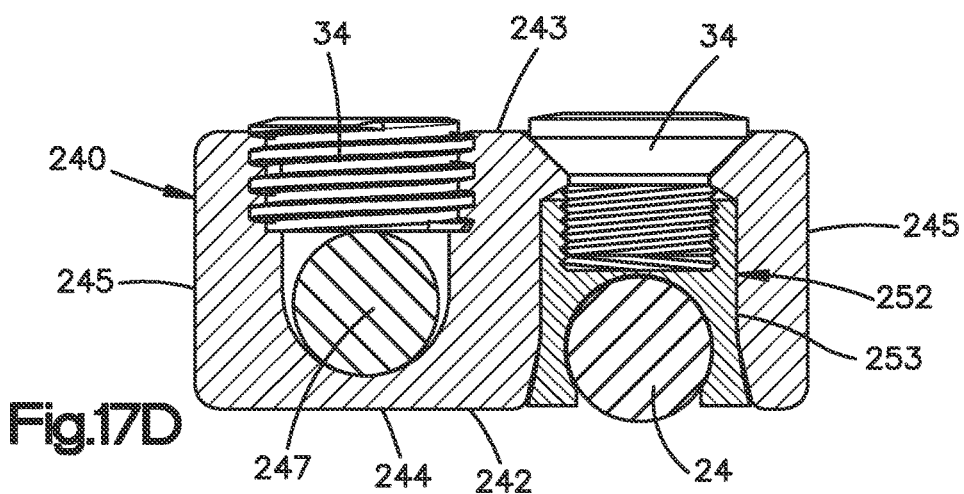

REVISION CONNECTOR FOR SPINAL CONSTRUCTS

CROSS-REFERENCE TO RELATED APPLICATIONS

This is a continuation of U.S. patent application Ser. No. 16/140,680 filed Sep. 25, 2018, which is a continuation of U.S. patent application Ser. No. 12/760,816, filed Apr. 15, 2010, which claims the benefit of U.S. Provisional Application Ser. No. 61/169,336, filed Apr. 15, 2009, the disclosures of both of which are hereby incorporated by reference as if set forth in their entirety herein.

TECHNICAL FIELD

The present invention relates generally to orthopedics, and in particular relates to implants and methods for revising existing posterior pedicle screw assemblies to additional levels.

BACKGROUND

The options that exist for revising and/or extending a posterior pedicle screw and rod construct in a patient are limited. Patients who have undergone previous spinal surgery often develop symptoms in adjacent spinal levels, which often cause pain and require additional surgery. Such additional spine surgeries often require existing hardware constructs to be extended one or more additional spinal levels. In such cases, a surgeon must decide if he can 1) extend the construct using the same hardware as the patient's existing hardware, 2) extend the construct using different hardware while leaving some of the patient's existing hardware in tact, or 3) remove all of the patient's existing hardware and replace it with new hardware, including the new spinal levels to be instrumented. Several disadvantages, however, characterize these approaches.

First, the patient's existing hardware must be identified via X-rays or fluoroscopy and, once identified, the surgeon must determine if the same make and model of hardware is available to the hospital or still on the market. The surgeon must also determine if his experience will allow him to revise and the existing hardware and/or add on new hardware, as some existing hardware systems are more difficult to revise or install. Based on these determinations, the surgeon may decide to revise using new hardware. Although a surgeon can choose the hardware of his choice, a connection between the existing hardware and the new hardware must be made, most often accomplished by removing or cutting the spine fixation rod from the superior most pedicle screw, replacing it with a new pedicle screw, and extending the construct. Concerns exist, however, that such a technique may disturb certain spinal levels that were previously asymptomatic and, thus, results in pain that previously did not exist. Further, many pedicle screw systems are not compatible with one another, significantly limiting the new hardware options for adding to the existing construct. If the surgeon decides to remove all existing hardware and replace it with new hardware of his choice he again is disturbing some spinal levels that were previously asymptomatic. Each of these options for adding and replacing hardware is time-consuming, especially if the surgeon is unfamiliar with the patient's existing hardware.

SUMMARY

In accordance with one embodiment, a revision connector is configured to couple a new spine fixation rod to a previously implanted spine fixation rod that is secured to a plurality of vertebrae. The revision connector includes a body having a first head and a first rod receiving channel extending into the first head, and a second head and a second rod receiving channel extending into the second head. The first and second channels are configured to receive respective fixation elements therein.

BRIEF DESCRIPTION OF THE SEVERAL VIEWS OF THE DRAWINGS

The foregoing summary, as well as the following detailed description of preferred embodiments of the application, will be better understood when read in conjunction with the appended drawings. For the purposes of illustrating the revision connector devices of the present application, there is shown in the drawings preferred embodiments. It should be understood, however, that the application is not limited to the precise arrangements and instrumentalities shown. In the drawings:

FIG. 1B is a perspective view of one of the bone fixation elements illustrated in FIG. 1A constructed in accordance with one embodiment, including an anchor seat, a bone anchor, a collet, and a locking cap;

FIG. 2 is a perspective view of the spine fixation rod illustrated in FIG. 1A;

FIG. 3 is a perspective view of the bone anchor illustrated in FIG. 1B;

FIG. 6 is a perspective view of the collet illustrated in FIG. 1B;

FIG. 7A is a sectional side elevation view of the bone fixation element illustrated in FIG. 1B taken along line 7A-7A, with the locking cap removed, to illustrate a pedicle screw assembly;

FIG. 7B is a sectional side elevation view similar to FIG. 7B, but showing a spine fixation rod extending through the anchor seat, and a locking cap affixed to the anchor seat;

FIG. 11B is a perspective view similar to FIG. 9, but showing a revision connector system including the revision connector illustrated in FIG. 10 secured between a new spine fixation rod to the previously implanted spine fixation rod;

FIG. 14B is a schematic elevation view of the first connector body illustrated in FIG. 14A;

FIG. 14C is a schematic elevation view similar to FIG. 14B, but showing the connector body constructed in accordance with an alternative embodiment;

FIG. 14D is a top plan view of the revision connector shown in FIG. 14C in accordance with one embodiment;

FIGS. 16A-D are schematic views illustrating a method for assembling the revision connector system illustrated in FIG. 14A;

FIG. 17B is a perspective view of the second revision connector system illustrated in FIG. 17A with the spine fixation rods removed;

FIG. 17C is an end elevation view of the second revision connector system illustrated in FIG. 17B, showing insertion of the previously implanted spine fixation rod;

FIG. 17D is an end elevation view of the second revision connector system illustrated in FIG. 17C, showing the previously implanted spine fixation rod secured in the second revision connector body.

DETAILED DESCRIPTION

Figure 1A:
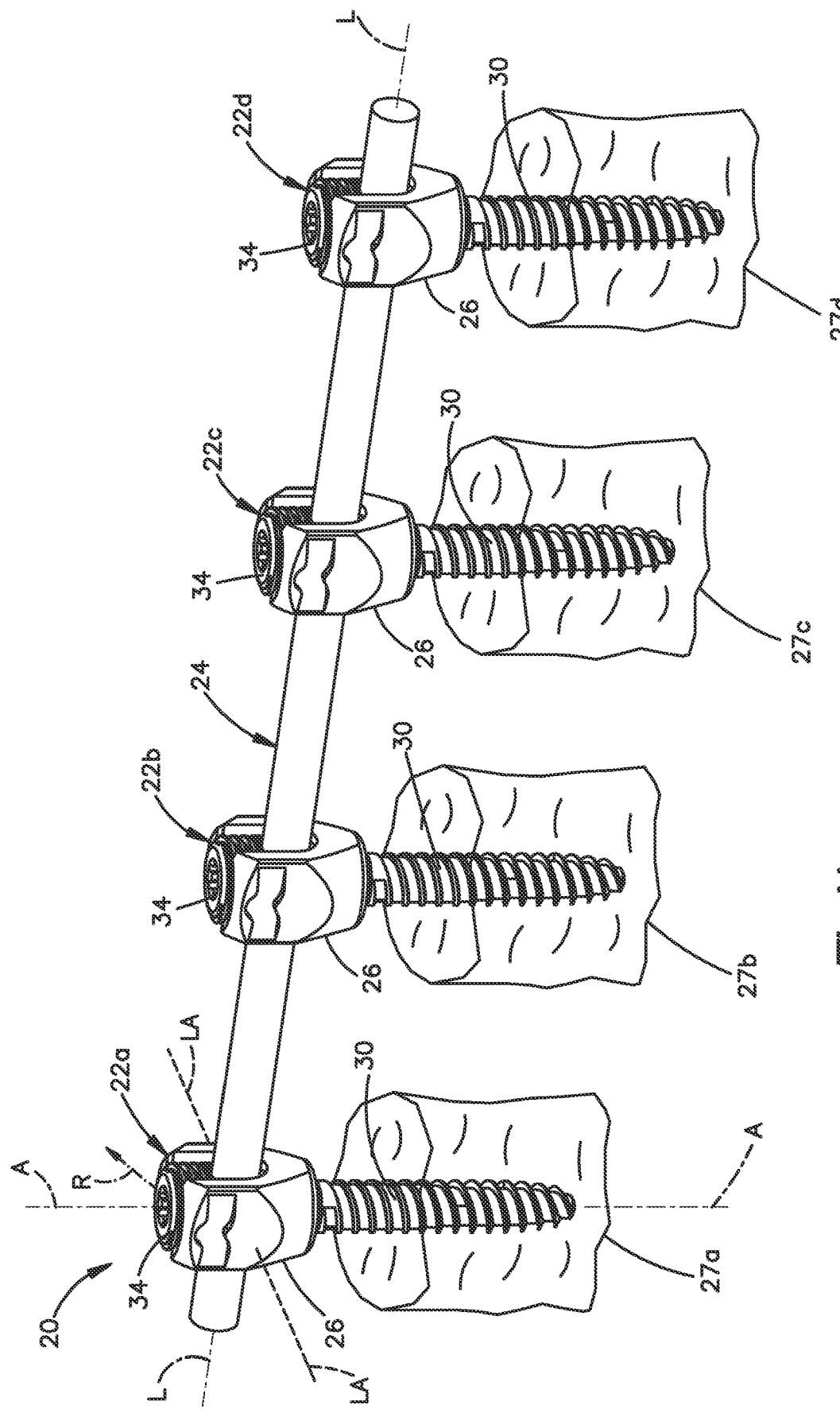
FIG. 1A is a perspective view of a bone fixation assembly constructed in accordance with one embodiment including a plurality of bone fixation elements connected to a previously implanted spine fixation rod, and illustrated schematically as each being previously secured to a vertebra.

Certain terminology may be used in the following description for convenience only and should not be considered as limiting in any way. For instance, a bone fixation assembly 20 includes one or more bone fixation elements 22, and four bone fixation elements 22A-D as illustrated in FIG. 1A. As shown in FIG. 1B, each bone fixation element 22 extends vertically along an axial direction A, and generally horizontally along a radial direction R that extends perpendicular to the axial direction A. Thus, the radial direction R includes a longitudinal direction L and a lateral direction LA that extends perpendicular to the longitudinal direction L. It should be appreciated that the directional terms "longitudinal," "lateral," can likewise apply to the bone fixation assembly 20 as extending horizontally, and the directional term "transverse" can refer to a vertical direction. The bone fixation element 22 defines an upper or posterior end 21 and a lower or inferior end 23, such that the directional terms "upper" and "lower" and derivatives thereof refer to a direction from the lower end 23 towards the upper end 21, and from the upper end 21 towards the lower end 23, respectively.

The words "inward," "outward," "upper," "lower," "distal," and "proximal," refer to directions toward or away from, respectively, the geometric center of the bone fixation assembly 20 and its components. The words, "anterior", "posterior", "superior," "inferior" and related words and/or phrases designate preferred positions and orientations in the human body to which reference is made and are not meant to be limiting. It should further be appreciated that while round structures define diameters as described herein, the round structures could be replaced with alternative (e.g., polygonal) structures which would define alternative cross-sectional dimensions opposed to diameters. The term "diameter" as used herein is intended to include all such alternatives unless otherwise specified. The terminology includes the above-listed words, derivatives thereof and words of similar import.

It should be appreciated that the directional terms are used herein with reference to the orientation of the bone fixation assembly 20 and its components as illustrated, and that the actual orientation of the bone fixation assembly 20 and its components may change during use. For instance, the axial direction is illustrated as extending along a vertical direction, and the radial direction is illustrated as extending along a horizontal direction, however the directions that encompass the various directions may differ during use, depending, for instance, on the desired orientation of the bone fixation assembly 20 during use. Accordingly, the directional terms are used herein merely for the purposes of clarity and convenience only, in a non-limiting manner.

Referring now to FIG. 1A, the bone fixation assembly 20 includes a plurality of bone fixation elements, such as bone fixation elements 22A-D, connected by a spine fixation rod 24 that extends along a longitudinal axis L. The bone fixation elements 22A-D each include a bone anchor 30 that is implanted (e.g., screwed) into a corresponding vertebra 27A-D. Unless otherwise specified, the bone fixation assembly 20 and its components can be made from titanium-aluminum-niobium alloy (TAN), implant-grade 316L stainless steel, or any suitable alternative implant-grade material.

With continuing reference to FIG. 1A, the bone fixation elements 22A-D will be described as and may be generally implanted in the spine, for instance at the pedicle portion of a lumbar, thoracic, or cervical vertebral body. In this regard, when the bone fixation elements 22A-D are joined by the rod 24, the assembly 20 fixes the relative position of the vertebrae (illustrated schematically at 27A-D). Accordingly, the bone fixation elements 22A-D can be referred to as spine fixation elements or pedicle screw assemblies, the spine fixation rod 24 can be referred to as a spine fixation rod, and the bone fixation assembly 20 can be referred to as a spine fixation assembly. However, it should be appreciated that the bone fixation assembly 20 can also be used for fixation of other parts of the body, such as joints, long bones, or bones in the hands, face, feet, extremities, cranium, and the like.

As shown in FIG. 2, the spine fixation rod 24 is elongate along a longitudinal axis L, and includes a body 25 that is cylindrical or tubular in shape. The longitudinal axis L extends generally in a cranial-caudal direction when the bone fixation assembly is affixed to the spine. The rod body 25 may include, but is not limited to, a solid body, a non-solid body, a flexible or dynamic body, or the like, and can assume any alternative shape as desired. It should thus be appreciated that the bone fixation assembly 20 is not limited in use to any particular spine fixation rod 24.

Referring now to FIG. 1B, the bone fixation elements 22A-D of the bone fixation assembly 20 will now be described with respect to the bone fixation element 22. In particular, the bone fixation element 22 generally includes a pedicle screw assembly 75, and a locking cap 34. The pedicle screw assembly 75 is illustrated as including a bone anchor seat 26, a collet 28 disposed inside the anchor seat 26, a bone anchor 30 (shown as a threaded bone screw) having a head portion 33 (see FIG. 3) attached to the collet 28. The locking cap 34 is installed in the anchor seat 26 at a location above the collet 28, such that the spine fixation rod 24 is located in a rod slot 36 that is disposed, and as illustrated defined, between the collet 28 and the locking cap 34.

Referring also to FIG. 3, the bone anchor 30 is configured as a bone screw, or pedicle screw, that includes an externally threaded shaft 31 coupled at its upper end to an enlarged curved head 33. The shaft 31 extends axially along a central axis B of rotation, and can define any suitable diameter, length, and thread design so as to engage the underlying bone, such as a vertebra 27. Alternatively, the shaft 31 can be unthreaded so as to define a pin or a nail if desired. Thus, one skilled in the art will appreciate that the bone anchor 30 is not limited to any particular type of shaft 31. The bone anchor 30 may also be cannulated and fenestrated such that openings extend radially outward from a central hollow channel in a cannulated shaft to urge fluid out of the bone anchor 30 during injection or draw fluid into the central hollow channel from the radial sides of the anchor during extraction of material adjacent the anchor if desired.

The bone anchor 30 further includes a vertically extending neck 35 connected between the shaft 31 and the head 33. The neck 35 is illustrated as extending axially in a direction parallel to axis B, and includes an outer neck surface 37 that defines a neck diameter, which is less than the diameter of the head 33.

The head 33 can define at least a partially spherical curvature, such as a semi-spherical curvature, or can alternatively define any suitable curvature as desired to facilitate rotation with respect to the collet 28 as is described in more detail below. The head 33 also includes a drive surface 39 configured to receive a corresponding tip of a drive tool, such as a screw driver configured to rotate the bone anchor 30 into engagement with the vertebrae 27 or other underlying bone surface. The drive surface 39 can define a hexagon, a star drive pattern, a Phillips head pattern, a slot for a screw driver, threads configured to receive corresponding threads of a threaded drive post, or any suitable drive tool engaging structure as desired.

Figure 4:
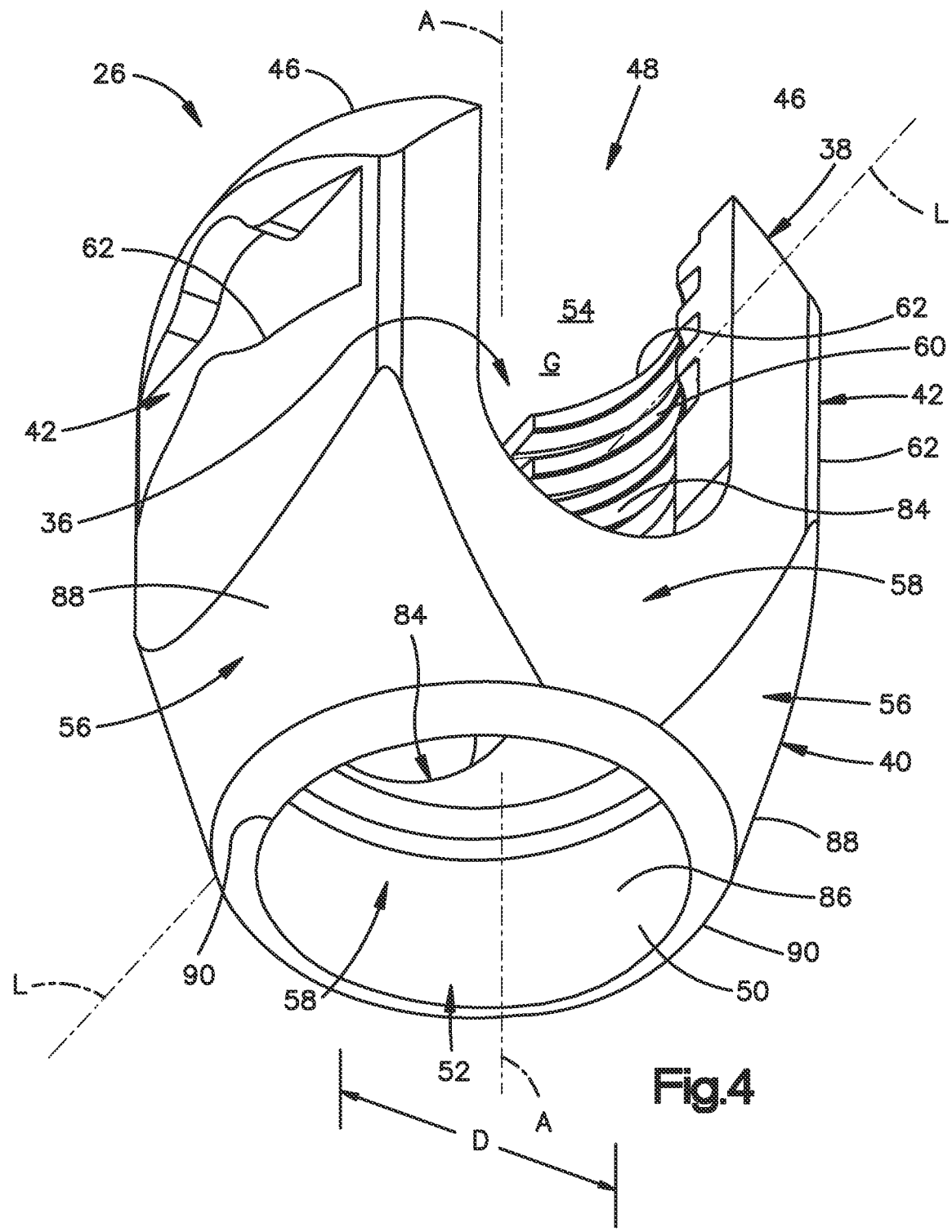
FIG. 4 is a perspective view of the anchor seat illustrated in FIG. 1B.

Referring now to FIG. 4, the anchor seat 26 includes an anchor seat body 38 that can be described as a generally cylindrical tubular body extending centrally along an axial axis A that extends generally in the anterior-posterior direction when the bone fixation element is implanted in the underlying vertebra. The body 38 includes a base 40 and a pair of spaced opposing arms 42 extending out (up in illustrated the orientation) from the base 40. The arms 42 can be substantially identically or identically constructed. The arms 42 define corresponding upper ends 46 that are also the upper ends of the body 38, and define an upper opening 48. The base 40 defines a lower end 50 that is also the lower end of the body 38, and defines a lower opening 52. The body 38 defines an axial bore 54 extending from the lower opening 52 to the upper opening 48.

The body 38 includes opposing support walls 56 and a pair of spaced opposing spacer walls 58 connected between the support walls 56. The support walls 56 can be substantially identically or identically constructed, and the spacer walls 58 can likewise be substantially identically or identically constructed. The arms 42 extend up from respective support walls 56, and can be shaped as desired. As illustrated, the arms 42 are arc-shaped with the axis of the arc passing through the plane of symmetry that bisects the anchor seat 26. Each arm 42 extends circumferentially about its axis less than 180°, such as between 60° and 150°, for instance approximately 90°. For instance, each arm 42 can extend circumferentially 90.5° about its axis.

Accordingly, a gap G extends circumferentially between adjacent circumferentially outer ends of the arms 42. The opposing gaps G are in alignment with the axial bore 54. The arms 42 can be disposed radially opposite each other such that the gaps G, in combination with the aligned portion of the axial bore 54, define a rod-receiving channel 36 that is sized and configured to receive the spine fixation rod 24 such that the spine fixation rod 24 extends through the bone fixation element 22. Thus, the gaps G are aligned in the longitudinal direction. The spine fixation rod 24 can thus extend through the opposing gaps G and the axial bore 54. The arms 42 define radially inner and outer surfaces 60 and 62, respectively. The inner surfaces 60 define threads 62, and are configured to threadedly receive the locking cap 34, as will now be described.

Figure 5B:
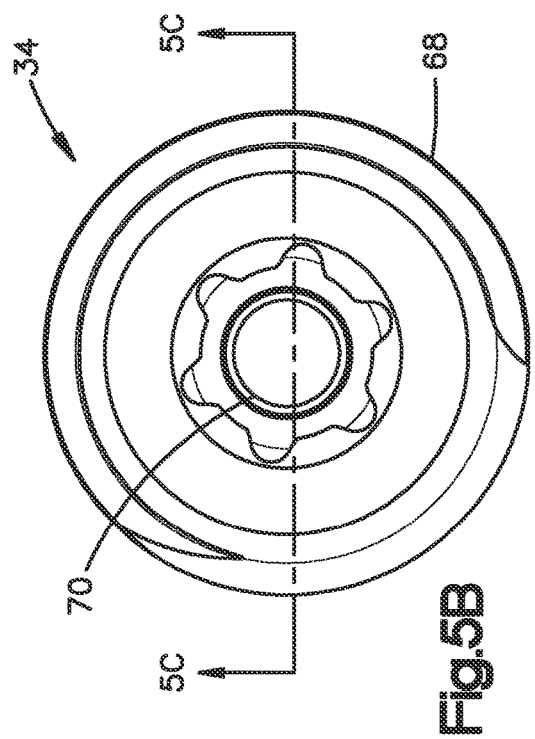
FIG. 5B is a top plan view of the locking cap illustrated in FIG. 5A.
Figure 5C:
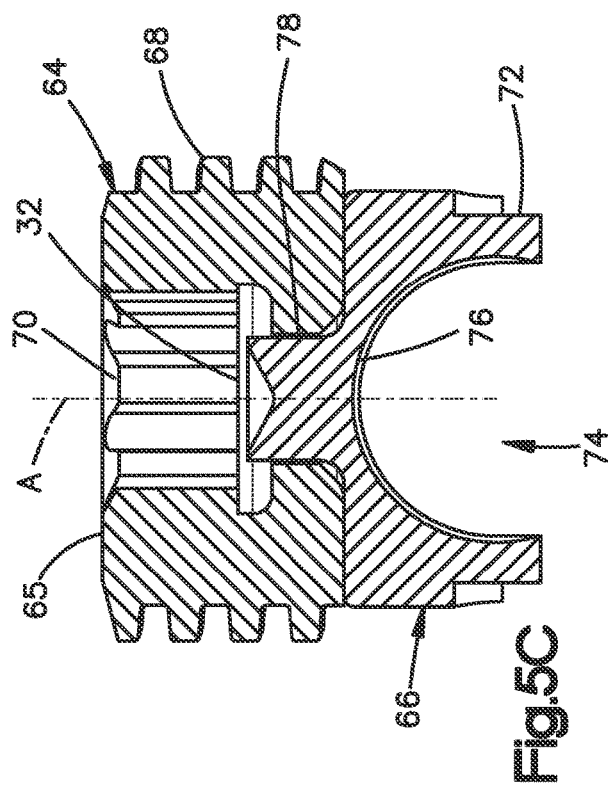
FIG. 5C is a sectional side elevation view of the locking cap illustrated in FIG. 5B.
Figure 5A:
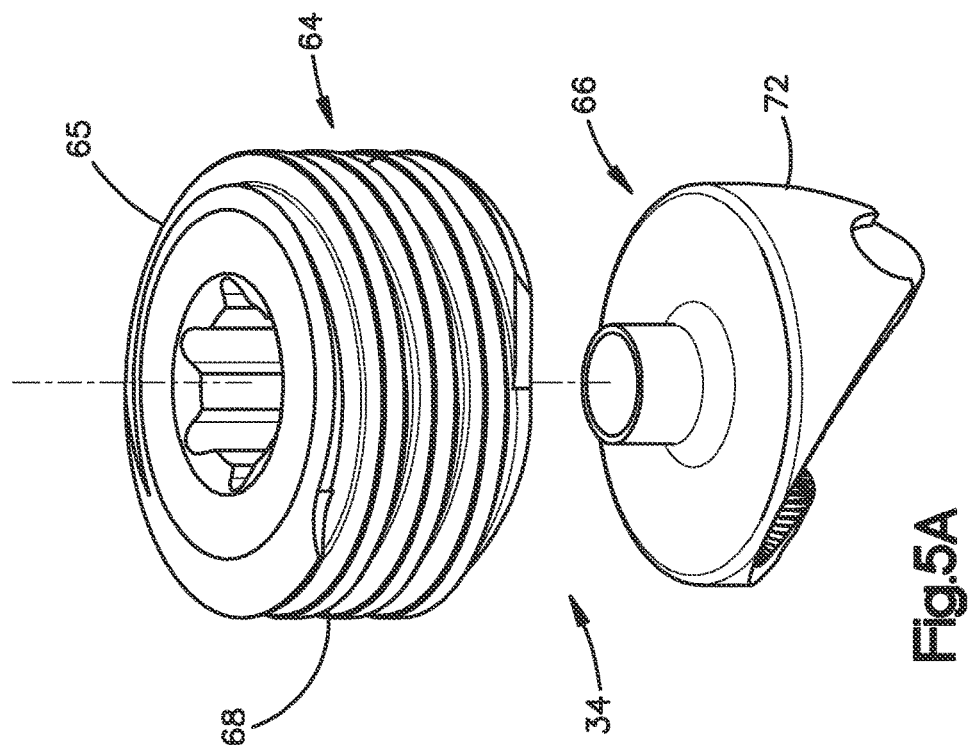
FIG. 5A is an exploded perspective view of the locking cap illustrated in FIG. 1B.

In particular, referring to FIGS. 5A-C, the locking cap 34 is illustrated as a set screw 64 and a saddle 66 operatively coupled to the set screw 64. The set screw 64 includes a generally cylindrical set screw body 65 having external threads 68 configured to threadedly engage the threads 62 formed on the inner surfaces 60 of the arms 42. In accordance with one embodiment, the threads 68 and 62 can incorporate inclined load flanks forming an angle with respect to the axis A of the bone fixation element 22. The load flanks may converge so that the top surface of the thread and the bottom surface of the thread converge. The angle may be between 0 degrees (0°) and 30 degrees (30°), and in one embodiment can be about five degrees) (5°). One skilled in the art will appreciate that the threads may take on any alternative form as desired, including negative load threads, perpendicular threads, buttress threads, or the like.

The externally threaded set screw 64 generally provides flexibility when inserting the spine fixation rod 24 into the anchor seat body 38 such that the spine fixation rod 24 need not be completely reduced or seated within the body 38 prior to engagement of the locking cap 34. The set screw 64 is configured to be tightened within the anchor seat 26 against the spine fixation rod 24. The locking cap 34 may be constructed as desired for this purpose including, but not limited to, an externally threaded cap, a quarter-turn or partial-turn locking cap, a two-piece screw set, or the like.

The set screw 64 is illustrated as including a drive surface 70 provided as an internal recess extending vertically down into the upper end of the screw 64. The drive surface has any suitable shape configured to cooperate with a corresponding drive tool for threadedly securing the set screw 64 onto the anchor seat body 38. The drive surface 70 can define any shape as desired, for instance an external hexagon, a star drive pattern, a Phillips head pattern, a slot for a screw driver, a threading for a correspondingly threaded post, or the like.

With continuing reference to FIGS. 5A-C, the saddle 66 includes a saddle body 72 having a transverse recess 74 extending up into the bottom end of the saddle body 72. The recess 74 can define a round surface that extends about a longitudinally extending axis, such that the recess 74 is configured to receive the spine fixation rod 24 at a rod-contacting surface 76. The rod-contacting surface 76 can include a desired surface finish that adds roughness, such as, for example, a knurl, bead blasting, grooves, or other textured finish that increases surface roughness and enhances rod push through strength.

The saddle 66 can be coupled to the set screw 64 in any desired manner, including adhesion, mechanical fastening, and the like. In the illustrated embodiment, the saddle 66 includes a stem 78 extending centrally upward from the saddle body 72. The stem 78 is configured to be received in a central bore 32 extending vertically into the lower end of the set screw body 65, and can be fastened within the central bore with a rivet 80 or other like fastener. Accordingly, the saddle 66 is rotatable relative to the set screw 64, such that the saddle 66 can self-align with the spine fixation rod 24 as the set screw 64 is being rotated with respect to the anchor seat 26, for instance when the locking cap 34 is being tightened against the spine fixation rod 24.

Referring again to FIG. 4, and as described above, the anchor seat body 38 includes a pair of spaced opposing support walls 56 and a pair of spaced opposing spacer walls 58 connected between the support walls 56. The arms 42 extend up from respective support walls 56, such that the spacer walls 58 are disposed between the arms 42. Each of the spacer walls 58 defines opposing upper ends 84 and lower ends 82 that can be shaped as desired. The upper ends 84 are round in accordance with the illustrated embodiment, such that the upper ends 84 and the circumferentially outer ends of the arms 42 are adjoined to generally define a U-shape from a horizontal view through the gaps G. Thus, the upper ends 84 define the lower end of the gaps G.

The upper ends 84 can be shaped to conform generally with the outer surface of the spine fixation rod 24, such that the upper ends 84 receive and engage the spine fixation rod 24 during use. Alternatively, the upper ends 84 can be spaced slightly below the upper surface of the collet 28, such that the collet 28 supports the spine fixation rod 24 during use, as will be described in more detail below.

The support walls 56 each define opposing inner and outer surfaces 86 and 88, respectively. The support walls 56 and the spacer walls 58 flare inward toward the central axis A in a downward direction from the arms 42, and terminate at respective lower ends 90. The inner surfaces 86 of the opposing support walls 56 and spacer walls 58 at the lower end 90 define a distance D therebetween that is less than the distance between opposing radially opposing inner surfaces 60 of the arms 42. The distance D can be less than or greater than the diameter of the head 33 of the bone anchor 30. The inner surfaces 86 flare radially inward toward the central axis A, and toward each other, along a downward direction, and are each connected to bottommost, and innermost, surfaces that define respective abutment walls 92.

Referring also to FIGS. 4B and 7A, each abutment wall 92 defines respective inner abutment surfaces 93 that in turn define a distance therebetween that is substantially equal to the diameter of the neck 35, such that the abutment walls 92 are configured to abut opposing abutment surfaces of the bone anchor, which are illustrated as opposing sides of the outer neck surface 37 when the bone anchor 30 is disposed in the anchor seat 26. Thus, the abutment walls 92 can prevent or limit pivoting of the bone anchor 30 relative to the anchor seat 26 in a desired plane.

Referring now to FIG. 6, the collet 28 includes a collet body 45 that defines a first or upper end 47 sized and configured to contact or support at least a portion of the spine fixation rod 24 when the rod is received within the rod-receiving channel 36, and a second or lower end 49 sized and configured to contact or otherwise engage, directly or indirectly, a portion of the bone anchor head 33. The collet body 45 is annular, and thus defines an axial bore 53 extending between and through the upper and lower ends 47 and 49. The axial bore 53 is aligned with the axial bore 54 when the collet 28 is installed in the anchor seat 26.

Referring to FIGS. 6 and 7A-B, the upper end 47 defines radially opposing upwardly facing seat portions 51 having a curvature or semi-spherical shape corresponding to the outer surface of the spine fixation rod 24, and is therefore configured to receive or otherwise support at least a portion (e.g., a lower portion) of the rod 24. The lower end 49 defines an inner surface 55 defining a curvature or semi-spherical shape corresponding to the outer surface of the anchor head 33, and is therefore configured to receive or otherwise engage at least a portion of the head 33, so that the head can rotate with respect to the collet 28 and the anchor seat 26, and can further pivot with respect to the collet 28 as permitted by the anchor seat 26. Because the bone anchor 30 can freely rotate about its axis of rotation B relative to the anchor seat 26, and thus the anchor seat 26 can likewise rotate about the bone anchor 30, the rod-receiving channel 36 can be aligned with the spine fixation rod 24 without advancing or withdrawing the bone anchor 30 in or out of the underlying bone. Thus, the bone anchor 30 can maintain a constant insertion depth in the underlying bone (e.g., vertebra 27) while adjusting the orientation of the rod-receiving channel 36.

Figure 8A:
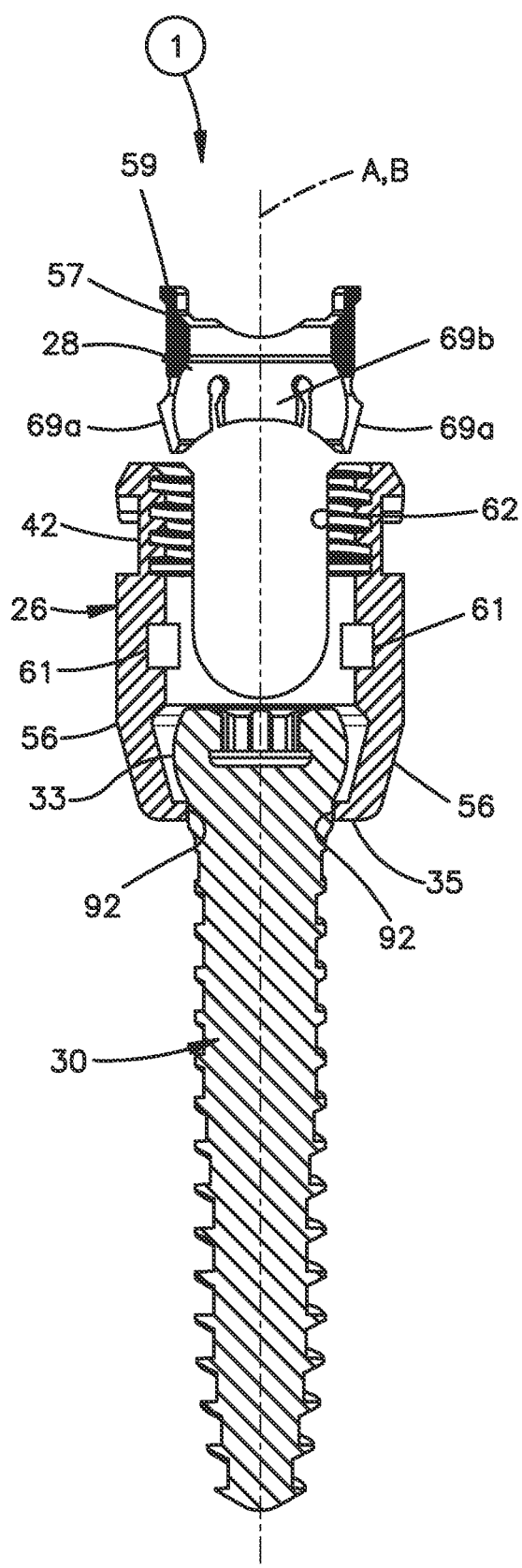
FIGS. 8A-D are schematic views illustrating a method for assembling the bone fixation element illustrated in FIG. 1A.
Figure 8B:
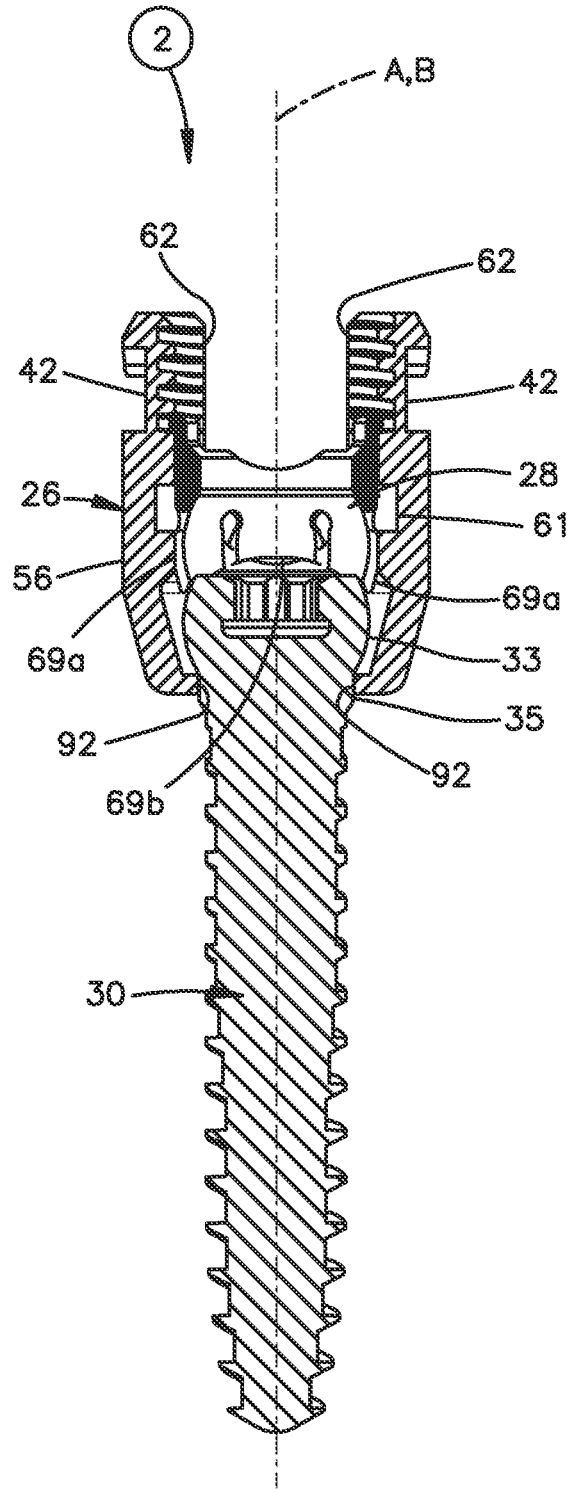
Figure 8C:
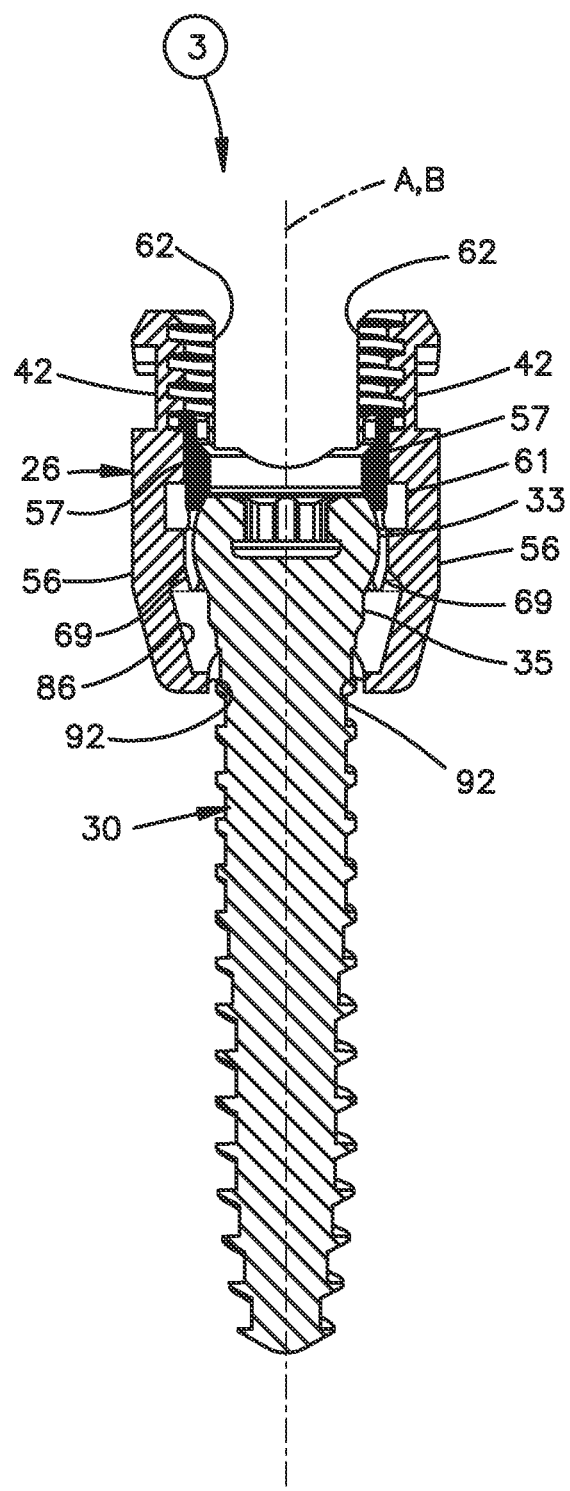
Figure 8D:
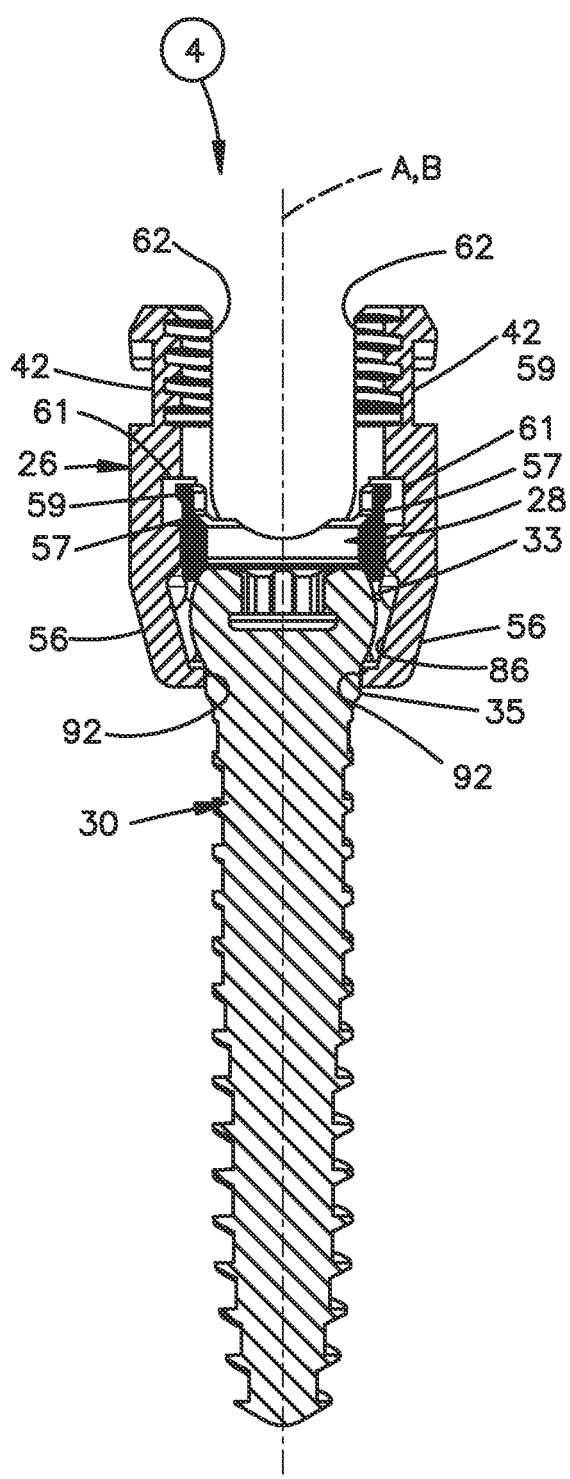

The collet 28 further includes a pair of flanges 57 extending up from the upper end 47 of the collet body 45 at a location radially between the seat portions 51. A locking lip 59 extends radially out from each flange 57. As best shown in FIG. 7A, the anchor seat 26 defines a pair of opposing recesses 61 (see FIG. 8A) formed radially in the opposing inner surfaces 86 of the support walls 56 at a location below the threaded inner surfaces 60 of the arms 42. During operation, the collet 28 can be inserted down into the anchor seat 26, thereby causing the flanges 57 to flex inwardly past the threaded inner surfaces 60, until the lips 59 clear the upper ends of the recesses 61, at which point the flanges 57 snap back out so that the lips 59 are disposed in the recesses 61. Interference between the lips 59 and the upper ends of the recesses 61 prevent the collet 28 from backing out through the upper end of the anchor seat 26. The recesses 61 further define a circumferential length substantially equal to that of the flanges 57 and locking lips 59, such that the collet 28 is rotationally fixed with respect to the anchor seat 26 in a position whereby the upper surface 47 is aligned with the spine fixation rod 24 when the spine fixation rod 24 is inserted into the anchor seat 26.

The lower end 49 of the collet 28 defines an outer diameter that is greater than the inner distance between the abutment walls 92. Accordingly, the collet 28 is unable to pass axially down through the lower end of the anchor body 26. The lower end 49 includes one or more slots 67 (illustrated as a plurality of slots) extending radially therethrough so as to define opposing pluralities of fingers 69 that are configured to pop over the head 33 of the bone anchor 30. When the collet 28 is disposed in the anchor seat 26 such that the lips 59 are disposed in the respective recesses 61, the fingers 69 are axially aligned with the abutment walls 92. Thus, as shown in FIGS. 7A-B, when the collet 28 and anchor 30 are installed in the anchor seat 24, the fingers 69 radially expand to conform with the outer surface of the anchor head 33 and the inner surfaces of the anchor seat 26. The inner diameters defined by the opposing fingers 69 are less than the outer diameter of the anchor head 33 to prevent the anchor 30 from being removed from the anchor seat 26 in an axially downward direction. The lower ends of the fingers 69 terminate at a location above the abutment walls 92. Accordingly, the fingers 69 do not interfere with the engagement between the anchor neck 35 and the abutment walls 92.

Referring now to FIGS. 8A-D, a method for assembling the pedicle screw assembly 75 includes at step 1, inserting the bone anchor 30 vertically down through the axial bore 54, such that the shaft 31 extends through the lower opening 52 of the lower end 50 of the anchor seat 26, and the anchor head 33 is disposed above the abutment walls 92. This method step for inserting the bone anchor 30 into the anchor seat 26 can thus be referred to as top-end loading of the bone anchor 30 into the anchor seat 26. Next, at step 2, the collet 28 is inserted into the axial bore 54 to a location whereby the locking lips 59 can engage the lowermost threads 62 of the inner surface 60 of the arms 42. Next, at step 3, an upward force can be applied to the bone anchor 30 so as to insert the anchor head 33 into the lower end 49 of the collet 28. The locking lips 59 of the collet 28 brace against the anchor seat 26 inside the threads 62 to prevent the upward force applied by the screw 28 from causing the collet 28 to back out of the upper opening of the anchor seat 26. At step 4, a downward force is applied to the collet 28, thereby inserting the locking lips 59 into the recesses 61 in the manner described above, and locking the anchor 30 and collet 28 in the anchor seat 26.

During use, because the bone anchor 30 is rotatable with respect to the collet 28 and the anchor seat 26, a driving tool can engage the drive surface 39 of the head 33 so as to insert the threaded shaft 31 into the underlying bone, as shown in FIG. 1A. Next, as shown in FIGS. 8A-D, the anchor seat 26 can be rotated about axis A in the direction of Arrow R about the full 360° range of angles so as to align the rod-receiving channel 36 with the longitudinal axis of the spine fixation rod 24. Once the bone anchor 30 has reached a desired depth in the underlying vertebra, the spine fixation rod 24 can be inserted into the pedicle screw assembly 75. In particular, the spine fixation rod 24 is inserted into the axial bore 54 either horizontally through the gaps G, or vertically down into the axial bore 54. It should be appreciated that the spine fixation rod 24 will be seated in the upper end 47 of the collet 28.

With continuing reference to FIGS. 8A-D, once the rod 24 is installed in the pedicle screw assembly 75, the locking cap 34 can be attached to the assembly 75 so as to fully assemble the anchor assembly 22. In the illustrated embodiment, the external threads 68 of the set screw 64 are rotated within the inner threads 62 of the anchor seat arms 42, thereby causing the set screw and saddle 66 to move axially down in the axial bore 54. As the saddle 66 approaches the spine fixation rod 24, the saddle 66 is rotated with respect to the set screw 64 so as to bring the rod-contacting surface 76 into alignment with the spine fixation rod 24. Once the saddle 66 is aligned with the spine fixation rod 24, the set screw 64 is continuously threadedly inserted into the bone anchor 26, such that the locking cap 34 can be tightened against the rod 24, thereby applying a downward axial force to the rod 24. The locking cap 34 can be said to be in an initial position when installed in the locking cap 34 but before applying an axial force against the spine fixation rod 24. The axial force applied to the rod 24 by the locking cap 34 is transmitted to the collet 28, which causes the fingers 69 to ride along the inner surfaces 86 of the support walls 56 and spacer walls 58.

As the fingers 69 ride along the walls 56 and 58, they become radially inwardly displaced due to the inward flare of the inner surfaces of the walls 56 and 58, thereby radially biasing, or radially compressing, the fingers 69 against the anchor head 33. Increasing radial compression of the fingers 69 against the anchor head 33 causes frictional forces between the fingers 69 and the anchor head 33 that resist rotation of the anchor 30 about the axis A relative to the anchor seat 26, collet 28, and spine fixation rod 24. When the locking cap is fully tightened to a locked position, the resulting frictional forces prevent the anchor 30 from movement relative to the anchor seat 26, collet 28, and spine fixation rod 24. Thus, the locking cap 34 is configured to transmit a locking force onto the collet 28 and bone anchor 30 to fix or lock the position of the bone anchor 30 relative to the anchor seat 26 and spine fixation rod 24. It should thus be appreciated that the spine fixation rod 24 is thus implanted to the underlying vertebra that is engaged by the bone anchor 30.

It should be appreciated that the above-described method steps can be performed for each bone fixation element of the bone fixation assembly 20 as desired. Furthermore, it should be appreciated that the while the bone fixation elements 22a-d have been described as each including the pedicle screw assembly 75 described above, the bone fixation elements 22a-d can include any alternatively constructed pedicle screw assembly suitable for fixing the spine fixation rod 24 to the underlying vertebrae 27. For instance, the pedicle screw assembly 75 can be constructed so as to permit the bone anchor 30 to be implanted into underlying bone before the anchor head 33 is inserted into the collet 28. In one embodiment, the abutment walls 92 are slotted so as to expand over the anchor head 33. Accordingly, the anchor seat 26 and collet 28 can be popped onto the head 33 from above instead of inserting the anchor 30 down through the anchor seat 26 in the manner described above. The method step of popping the anchor seat 26 over the head 33 can be referred to as bottom-end loading of the anchor 30 into the anchor seat 26.

Figure 9:
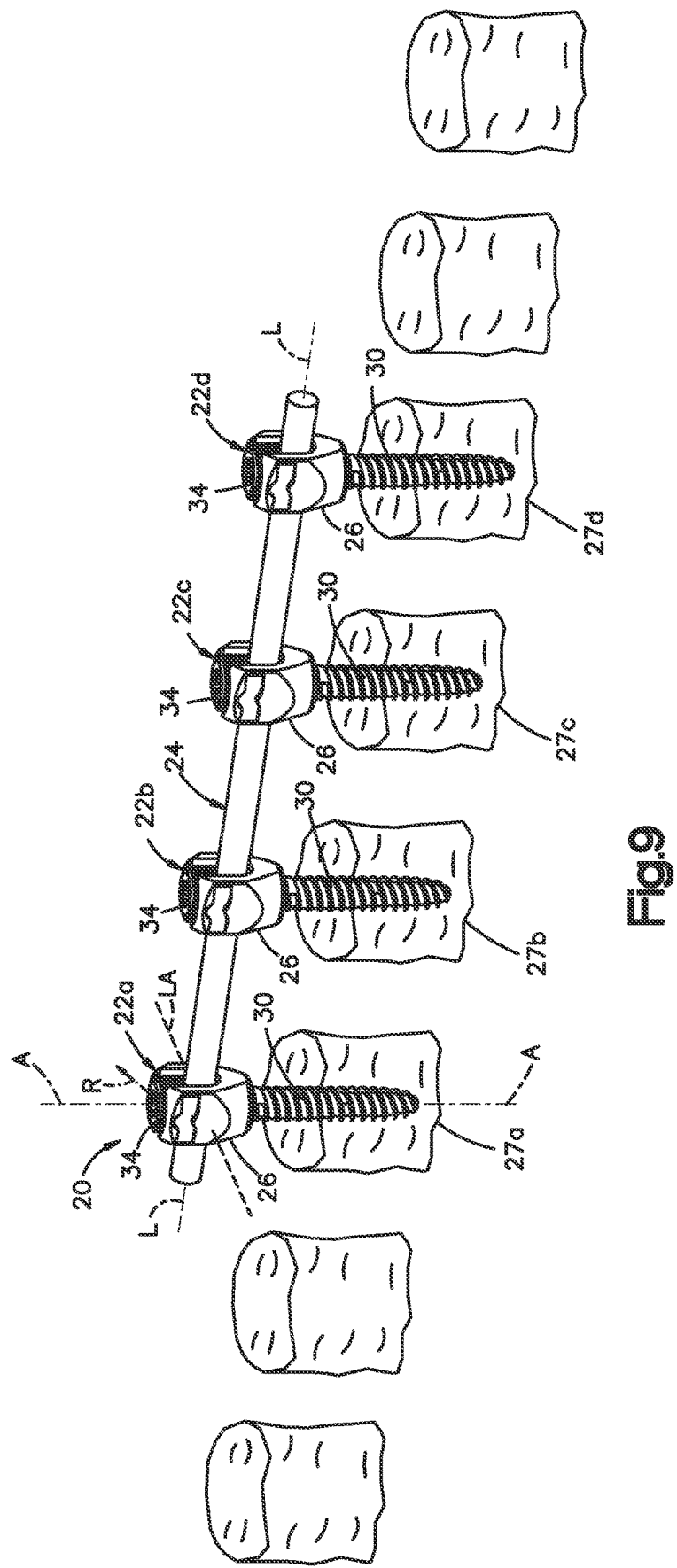
FIG. 9 is a perspective view similar to FIG. 1A, but showing a plurality of superior and inferior vertebrae with respect to the previously secured vertebrae.

Referring now to FIG. 9, it should be appreciated that the while the spine fixation rod 24 is implanted in a plurality of vertebrae 27a-d in the bone fixation assembly 20, it may become desirable at a future date to extend the bone fixation assembly 20 to affix at least one such as a plurality of vertebrae to the vertebrae 27a-d. For instance, it may be desirable to affix at least one such as a plurality of inferior vertebrae 27e-f to the vertebrae 27a-d. Alternatively or additionally, it may be desirable to affix at least one such as a plurality of superior vertebrae 27g-h to the vertebrae 27a-d. Thus, the spine fixation rod 24 can be referred to herein as a previously implanted spine fixation rod. As illustrated, the vertebra 27a is the cranial-most vertebra that is secured to the spine fixation rod 24, and the vertebra 27d is the caudal-most vertebra that is secured to the spine fixation rod 24. The vertebra 27h is superior to the vertebra 27a, and the vertebra 27g is superior to the vertebra 27h. The vertebra 27e is inferior to the vertebra 27d, and the vertebra 27f is inferior to the vertebra 27e. The vertebrae 27g-h and 27e-f can be referred to as new vertebrae.

Figure 10A:
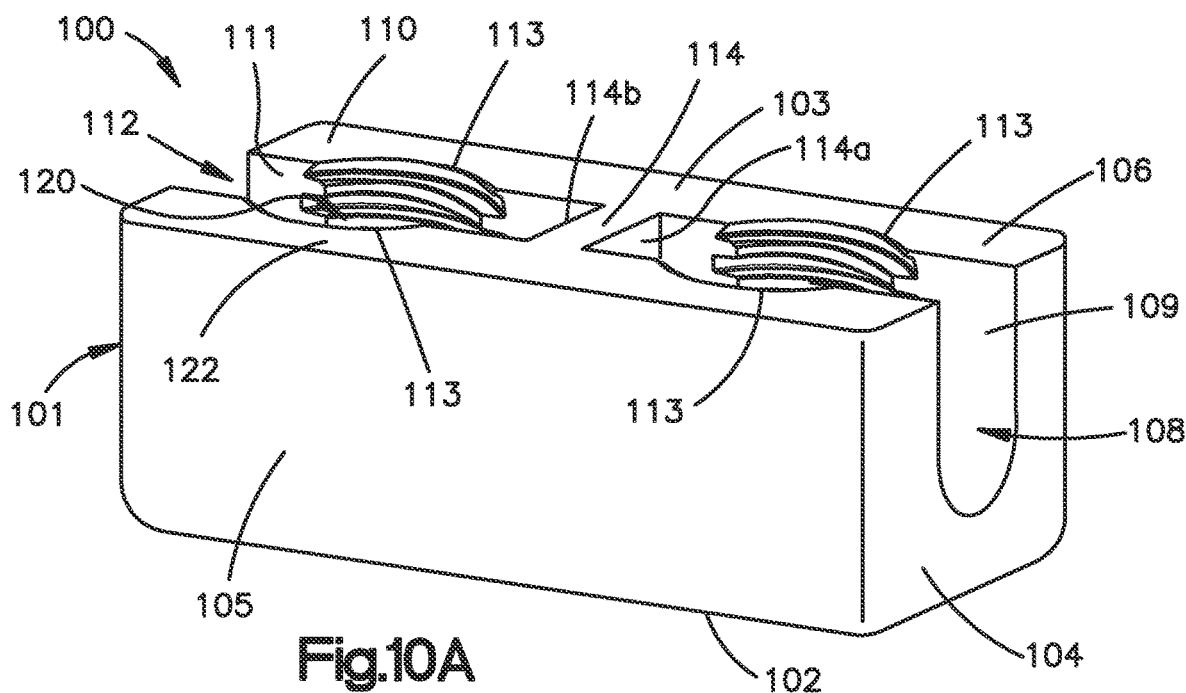
FIG. 10A is a perspective view of a revision connector constructed in accordance with one embodiment.
Figure 10B:
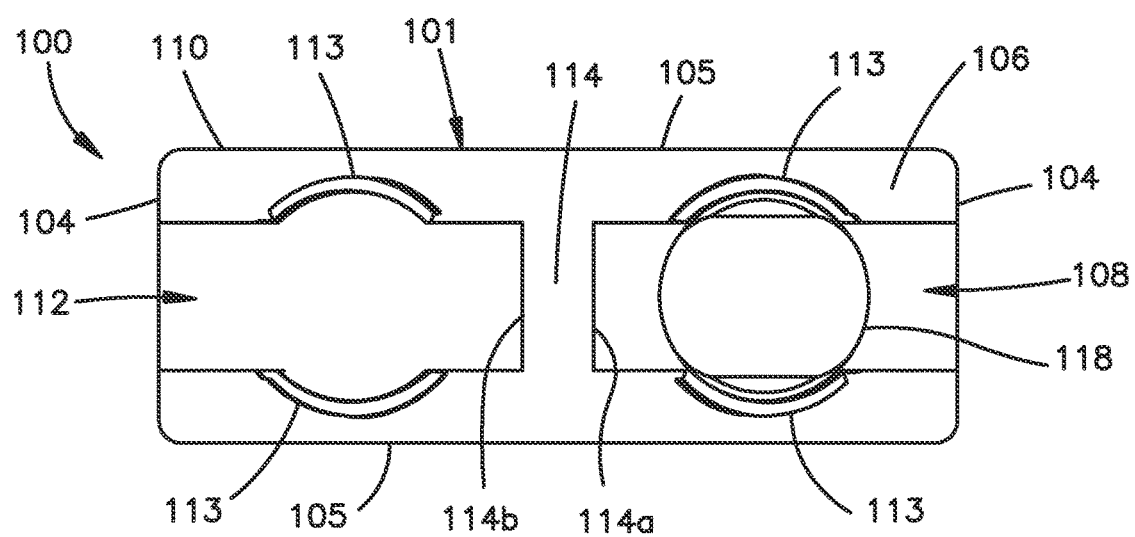
FIG. 10B is a top plan view of the revision connector illustrated in FIG. 10A.
Figure 10C:
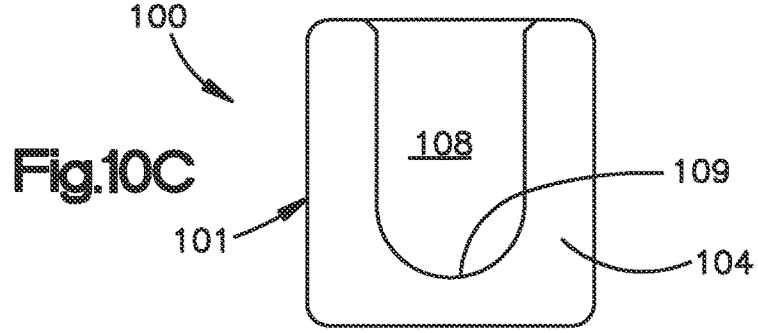
FIG. 10C is an end elevation view of the revision connector illustrated in FIG. 10A.

Referring now to FIGS. 10A-C, a revision connector 100 is configured to couple a new spine fixation rod to the previously implanted spine fixation rod 24. The revision connector 100 includes a body 101 having an inner vertebral facing surface 102, an opposing outer surface 103 separated from the inner surface 102 along the axial direction A, opposing end surfaces 104 connected between the inner and outer surfaces 102 and 103 and spaced apart in the longitudinal direction, and opposing side surfaces 105 connected between the inner and outer surfaces 102 and 103, further connected between the end surfaces 104, and spaced apart in the lateral direction. It should be appreciated that, depending on the orientation of the connector body 101, one of the end surfaces 104 can be positioned as a superior end surface, while the other end surface 104 can be positioned as an inferior end surface once the connector 100 has been implanted. While the connector 100 is illustrated having a generally rectangular structure having the discrete surfaces 102-105, it should be appreciated that any shaped structure can define the surfaces as described herein as desired, even though the surfaces may be curved or angled with respect to the longitudinal, axial, and/or lateral directions.

The revision connector 100 is a dual head connector, such that the body 101 defines a first head 106 and a first rod receiving channel 108 extending into the first head 106, and a second head 110 and a second rod receiving channel 112 extending into the second head 110. The rod receiving channels 108 and 112 include respective round inner surfaces 109 and 111 that can be contoured to generally conform with and support the outer diameter of a new spine fixation rod 116 (see FIG. 11B) and the previously implanted spine fixation rod 24. It should be appreciated that the previously implanted rod 24 and the new rod 116 can be more broadly construed as fixation elements. As illustrated, the heads 106 and 110 are longitudinally offset (along a direction substantially parallel to the previously implanted spine fixation rod 24). The revision connector 100 can further include a divider wall 114 that separates the heads 106 and 110, and further defines opposing stop surfaces 114a and 114b in the rod receiving channels 108 and 112, respectively.

At least one or both of the heads 106 and 110 is constructed generally as described above with respect to the bone fixation elements 22. For instance, as illustrated, the revision connector 100 includes opposing threaded arcuate cutouts 113 extending axially into the body 101 at the second head 110. The cutouts 113 are configured to receive a locking cap such as the locking cap 34 described above. Thus, the body 101 of the second head 110 is constructed generally as described above with respect to the spaced opposing arms 42 that define a rod receiving channel 36.

The body 101 of the second head 110 likewise defines the rod receiving channel 112. Furthermore, the body 101 defines a lower opening 118 that extends axially between and through the inner surface 102 and the rod receiving channel 108 in a direction substantially transverse to the rod receiving channel 108, generally as described above with respect to the lower opening 52. Thus the lower opening 118 is sized to receive and retain a bone anchor 30 in the manner described above. As will be appreciated from the description below, the opening 118 is in operative alignment with the spine fixation rod that extends into the corresponding channel. That is, the opening 118 can retain the bone anchor 30 that fixes the spine fixation rod to the underlying vertebra. The body 101 further defines an axial bore 120 extending through the second head 110 in alignment with the lower opening 118. The axial bore 120 is generally as described above with respect to the axial bore 54. Thus, it should be appreciated that the first head 106 defines an anchor seat 122 generally as described above with respect to the anchor seat 26. The connector body 101 can thus also be referred to as an anchor seat body, and the head 110 can be referred to as an anchor seat.

The body 101 of the first head 106 is generally as described above with respect to the second head 110, however, the first head 106 does not define a lower opening extending between and through the inner surface 102 and the rod receiving channel 108. Thus, the first head 106 is not configured to support a bone anchor. Alternatively, it should be appreciated that the first head 106 can be constructed as described with respect to the second head 110 so as to allow either head to secure directly to an underlying vertebra via a bone anchor.

As illustrated, the first fixation rod receiving channel 108 extends from the respective end surface 104 of the first head 106 to the stop surface 114a of the divider wall 114, and the second fixation rod receiving channel 112 extends from the respective end surface 104 of the second head 110 to the stop surface 114b of the divider wall 114. Alternatively, the connector body 101 can be devoid of the divider wall 114, such that the rod receiving channels 108 and 112 are continuous with each other. Furthermore, while the heads 106 and 110, and the respective channels 108 and 112, are in lateral alignment with each other, they could alternatively be laterally offset as described in more detail below. Because the heads are longitudinally aligned, each head 106 and 110 has only one end surface that collectively define the end surfaces 104 of the connector body 101. In embodiments where the heads 106 and 110 are laterally adjacent, each head 106 and 110 has only one side surface 105 that collectively define the opposing side surfaces 105 of the connector body 101.

Referring now to FIGS. 11A-12C, a revision connector system 121 can include the revision connector 100, the new spine fixation rod 116, a bone anchor such as the bone anchor 30 as described above, one or more collets such as the collet 28 constructed as described above configured to retain the bone anchor 30, and one or more locking caps such as the locking cap 34 constructed as described above. Unless otherwise indicated, the revision connector system 121 and its components can be made from a titanium-aluminum-niobium alloy (TAN), implant-grade 316L stainless steel, or any suitable alternative implant-grade material The collet is configured to capture and lock the head of the bone anchor 30 by popping the connector body 101 down onto the bone anchor 30 so as to "pop" the collet onto the head of the bone anchor 30 as described above. Alternatively, the collet can be configured to couple to the bone anchor 30 by loading the bone anchor 30 down through the top of the connector 100 so that the shaft of the anchor extends through the opening 118 prior coupling the bone anchor 30 to the underlying vertebral body. In an alternative embodiment, the collapsible collet can be replaced by other elements that are configured to be disposed interior to rod-to-screw connectors and serve to securely connect the head of the bone anchor 30 to the connector body 101. The locking caps 34 are configured to secure the previously implanted rod 24 and the new rod 116 to the connector 100, and to secure the bone anchor 30 to the connector 30.

It is appreciated that the previously implanted spine fixation rod 24 may define a range of different diameters, as manufacturers often market spine fixation rods of differing diameters. Similarly, the pedicle screw assemblies 75 of the bone fixation elements 22A-D can assume the form of a variety of different makes and models. Likewise, the new spine fixation rod 116 can have a diameter that is substantially equal to, greater than, or smaller than, that of the previously implanted spine fixation rod 24. The connector 100 can be configured to secure the spine fixation rods 116 and 24 whether their diameters are the same or different. Likewise, pedicle screw assemblies that secure the new spine fixation rod 116 to underlying vertebrae can be constructed the same as or differently than the pedicle screw assemblies 75.

Figure 11A:
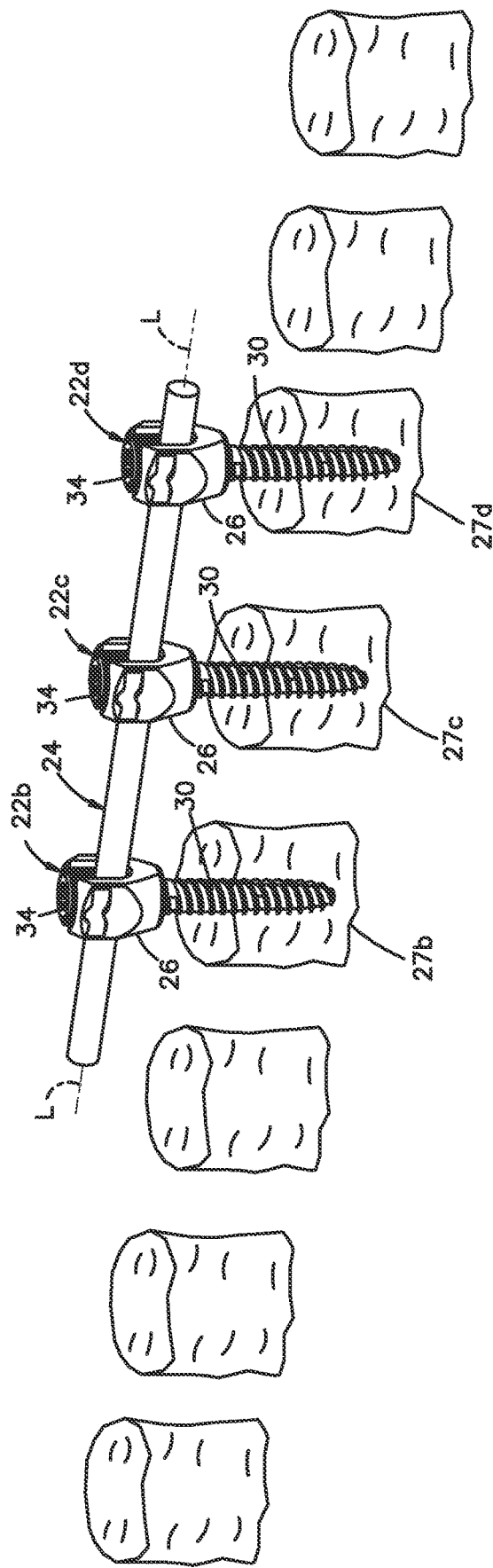
FIG. 11A is a perspective view similar to FIG. 9, but showing the previously implanted fixation rod cut.
Figure 12A:
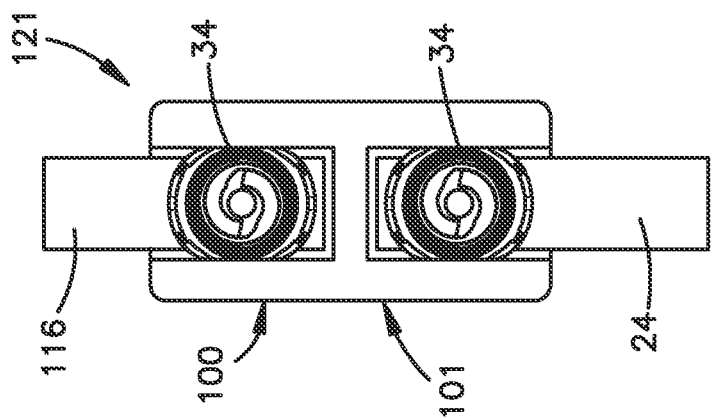
FIG. 12A is a schematic end elevation view of the revision connector illustrated in FIG. 11B.
Figure 12B:
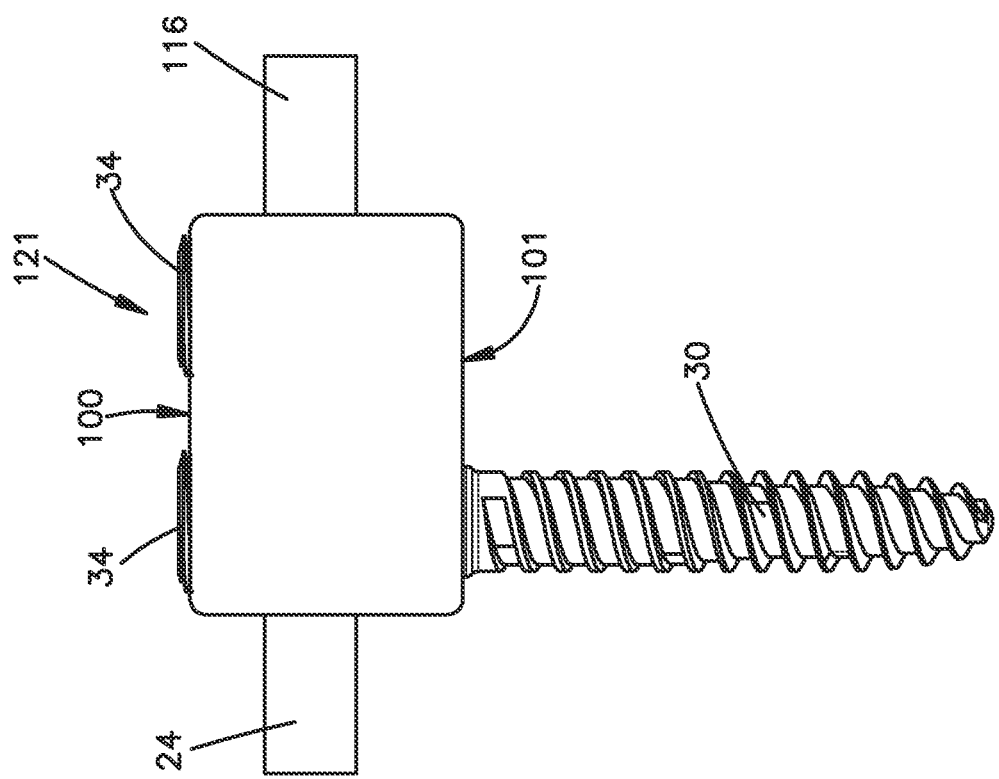
FIG. 12B is a schematic side elevation view of the revision connector illustrated in FIG. 12A.
Figure 12C:
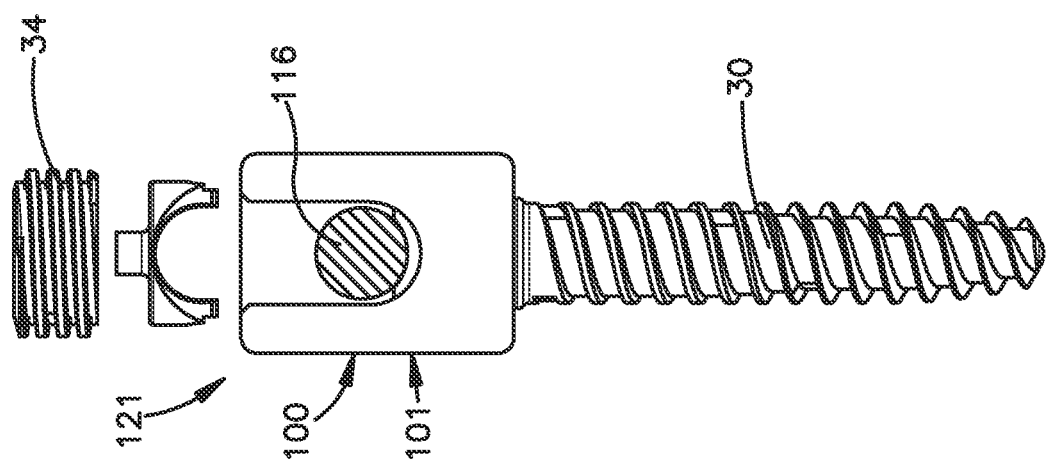
FIG. 12C is a schematic top plan view of the revision connector illustrated in FIG. 12A.

During operation, the revision connector system 121 can extend the previously implanted bone fixation assembly 20 by extending the previously implanted spine fixation rod 24 to other vertebrae. As illustrated in FIG. 11A, the previously implanted rod 24 is cut at a location between the outermost secured vertebra and the adjacent secured vertebra. The bone fixation element 22 associated with the outermost vertebra is then removed. For instance, as shown in FIG. 11A, when extending the spine fixation rod cranially, the spine fixation rod 24 is first cut between the cranial-most secured vertebra 27a and the adjacent vertebra 27b, and the bone fixation element 22a. When extending the spine fixation rod caudally, the spine fixation rod 24 is first cut between the caudal-most secured vertebra 27d and the adjacent vertebra 27c, and the bone fixation element 22d is removed. The bone anchor 30 is then implanted at or near the point from which the bone anchor portion of the bone fixation element 22a was removed, or into the vertebral body 27h adjacent (cranially) to the vertebral body 27a from which the bone fixation element 22a was removed.

The revision connector 100 is then placed such that the superior end of the previously implanted spine fixation rod 24 is disposed in the channel 108 of the first head 106, and the second head 110 is secured to the bone anchor 30. For instance, the bone anchor 30 can already be implanted in the underlying vertebra, such that the anchor seat 122 is popped over the anchor head 33 in the manner described above. Alternatively, the bone anchor 30 can be inserted longitudinally through the axial bore 120 in the manner described above, and subsequently affixed to the underlying vertebra. The newer rod 130 is then implanted and secured to a desirable number of at least one superior vertebral body, such as the superior vertebral bodies 27h and 27g, using a corresponding number of additional pedicle screw assemblies, such as pedicle screw assemblies 75 as described above. The inferior end of the new spine fixation rod 116, which extends over at least one superior vertebra to be secured, is then urged into the rod receiving channel 112 of the second head 110. The spine fixation rods 24 and 116 can be inserted until their terminal ends abut the respective stop surfaces 114a-b of the divider wall 114. Once the spine fixation rods are disposed in their respective rod receiving channels, the locking cap 34 can be threaded into the arcuate cutouts 113 so as to secure the previously implanted spine fixation rod 24 to the first head 106 in the channel 108, and to secure the new spine fixation rod 116 and the bone anchor 30 to the second head 110 in the channel 112.

To extend a previously implanted bone fixation assembly 20 caudally, as opposed to cranially, the new rod 116 is then implanted and secured to a desirable number of at least one inferior vertebral body, such as the inferior vertebral bodies 27e and 27f, using a corresponding number of additional pedicle screw assemblies, such as pedicle screw assemblies 75 as described above. The superior end of the new spine fixation rod 116 is then urged into the rod receiving channel 112 of the second head 110.

Figure 13A:
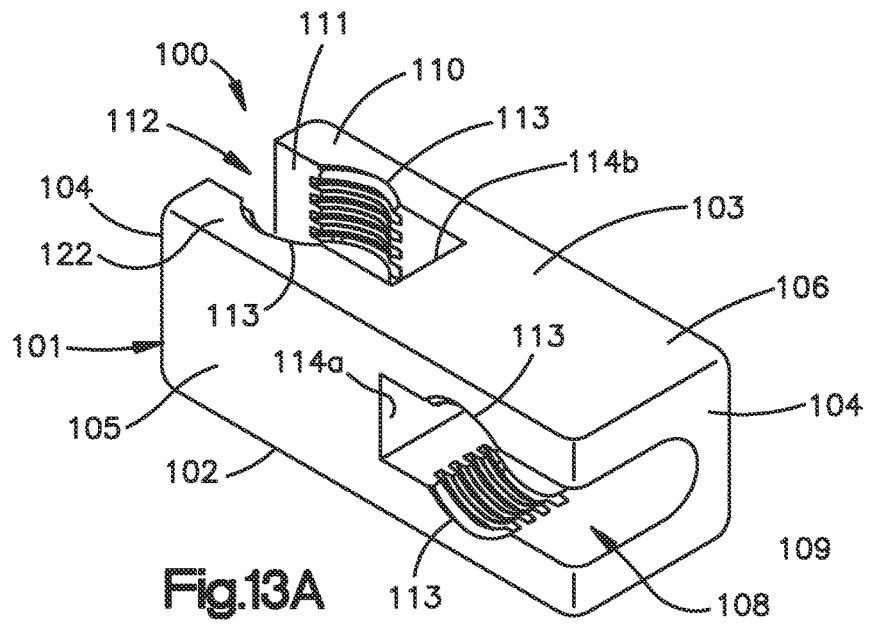
FIG. 13A is a perspective view of a revision connector constructed in accordance with an alternative embodiment.
Figure 13B:
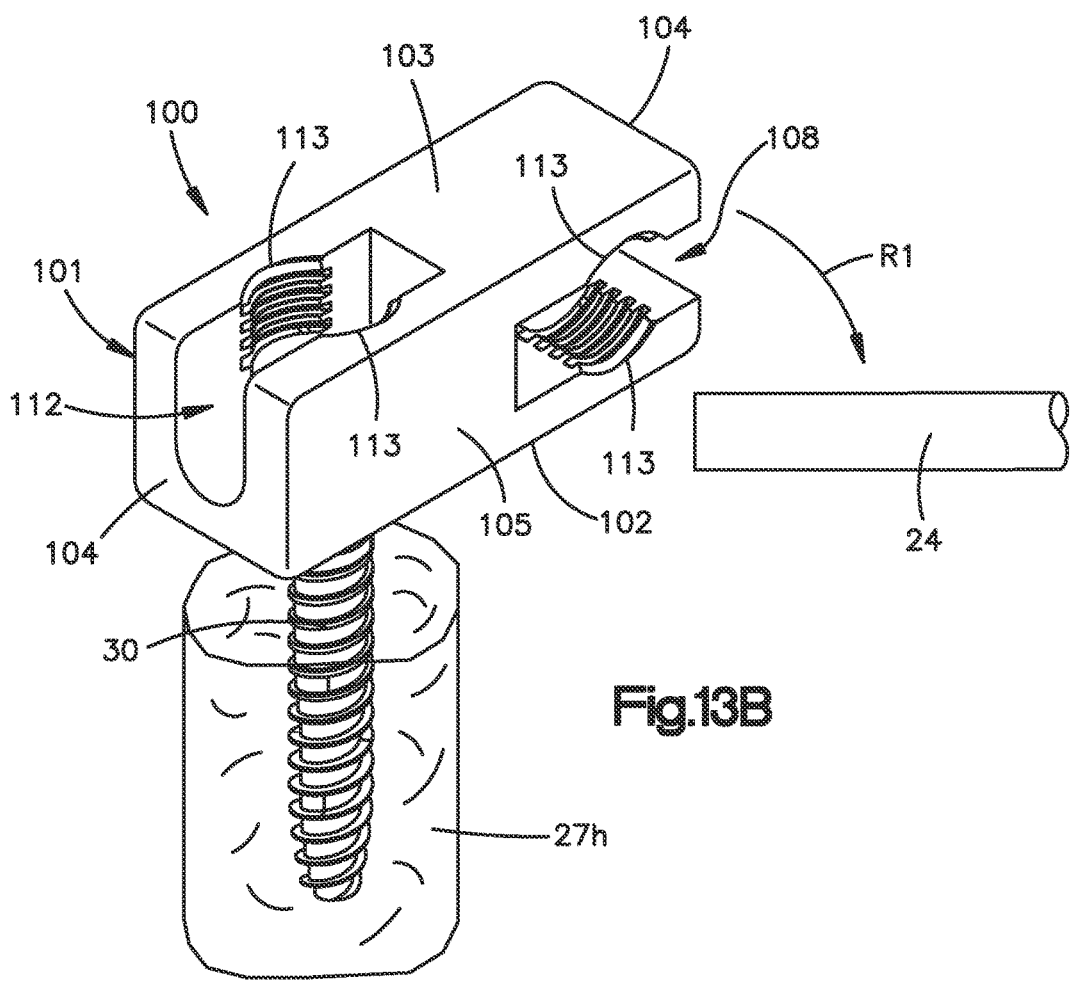
FIG. 13B is a perspective view showing a method for securing the revision connector illustrated in FIG. 13A to the previously implanted spine fixation rod.

While the channels 108 and 112 are illustrated as extending down through the outer surface 103 toward the inner surface 102 of their respective heads 106 and 110, it should be appreciated that at least one or both of the channels 108 and 112 could alternatively extend into one of the side surfaces 105 or the inner surface 102 unless otherwise indicated. For instance, referring to FIGS. 13A-B, the channel 108 of the first head 106 extends into one of the side surfaces 105. Thus, the opposed arcuate cutouts 113 extend laterally into the channel 108.

During operation, the bone anchor 30 is fastened to the underlying veretbra 27, such that the anchor head 33 is disposed in the second head 110. As described above, the anchor can be inserted down through the opening 118, or the second head 110 of the connector body 101 can be popped onto the head of the bone anchor 30. Once the revision connector 100 is coupled to the head of the bone anchor 30, and the previous rod 24 has been cut in the manner described above, the connector body 101 can be rotated through an angle about the central axis B of the bone anchor 30 along the direction R1 so as to guide the previously implanted spine fixation rod 24 into the channel 108 of the first head 106, thereby side-loading the rod 24 into the channel 108. The new rod 116 is then urged into the second head 110 of the revision connector 200, and the locking caps 34 can be tightened to secure the connector 200 to previously implanted rod 24, the new rod 116, and the bone anchor 30. The channel 108 of the first head 106 can be laterally offset with the channel 112 of the second head 110, or inline with the channel 112 of the second head 110.

Referring now to FIGS. 14A-16D, a revision connector system 221 can be provided that is configured to secure one or more new vertebrae to vertebrae that have previously been fixed using the previously implanted spine fixation rod 24 without cutting the spine fixation rod 24 as described above with respect to the revision connector system 121. The revision connector system 221 includes a revision connector 200, the new spine fixation rod 116, a bone anchor such as the bone anchor 30 as described above, one or more collets such as the collet 28 constructed as described above configured to retain the bone anchor 30, and one or more locking caps such as the locking cap 34 constructed as described above.

The revision connector 200 includes a first connector body 201 and a second body 240 that is coupled to the first body via a fixation element in the form of a linkage 247 that can be provided as a rod segment that can be integrally connected to the second body 240, and thus part of the second body 240, or discretely connected to the second body 240. The first body 201 defines an inner vertebral facing surface 202, an opposing outer surface 203 separated from the inner surface 202 along the axial direction A, opposing end surfaces 204 connected between the inner and outer surfaces 202 and 203 and spaced apart in the longitudinal direction, and opposing side surfaces 205 connected between the inner and outer surfaces 202 and 203, further connected between the end surfaces 204, and spaced apart in the lateral direction. It should be appreciated that, depending on the orientation of the first connector body 201, one of the end surfaces 204 can be positioned as a superior end surface, while the other end surface 204 can be positioned as an inferior end surface once the connector 200 has been implanted. While the connector 200 is illustrated having a generally rectangular structure having the discrete surfaces 202-205, it should be appreciated that any shaped structure can define the surfaces as described herein as desired, even though the surfaces may be curved or angled with respect to the longitudinal, axial, and/or lateral directions.

The first body 201 defines a first head 206 and a first rod receiving channel 208 extending into the first head 206, and a second head 210 and a second rod receiving channel 212 extending into the second head 210. The first rod receiving channel 206 extends into one of the side surfaces 205 of the first head 206, and the second rod receiving channel 210 extends into the outer surface 203 of the second head 210. The rod receiving channels 208 and 212 include respective round inner surfaces 209 and 211 that can be contoured to generally conform with the outer diameter of the new spine fixation rod 116 and the linkage. As illustrated, the heads 206 and 208 are laterally offset (along a direction angularly offset, and in particular substantially perpendicular, with respect to the previously implanted spine fixation rod 24). The revision connector 200 can further include stop surfaces 214a and 214b in the rod receiving channels 208 and 212, respectively.

At least one or both of the heads 206 and 210 is constructed generally as described above with respect to the first head 106. For instance, as illustrated, the revision connector 200 includes opposing threaded arcuate cutouts 213 extending axially into the body 201 at the first head 206. The cutouts 213 are configured to receive a locking cap such as the locking cap 34 described above. Thus, the body 201 of the first head 206 is constructed generally as described above with respect to the spaced opposing arms 42 that define a rod receiving channel 36. Because the body 201 is not directly connected to an underlying vertebra in accordance with one embodiment, the body 201 does not define a lower opening (such as opening 118 described above) that extend extends axially between and through the inner surface 202 and either rod receiving channel 208 or 212. Alternatively, it should be appreciated that either or both of the first and second heads 206 and 210 can include a lower opening such as opening 118 so as to allow either head to secure directly to an underlying vertebra via a bone anchor.

As illustrated, the first fixation rod receiving channel 208 extends into the side surface 205, and is elongate from the respective end surface 204 of the first head 206 to the stop surface 114a. The second fixation rod receiving channel 212 extends into the outer surface 203, and is elongate from the respective end surface 204 of the second head 210 to the stop surface 214b. Alternatively, the channels 208 and 212 could extend longitudinally entirely through to the connector body 201. The second channel 212 is laterally offset with respect to the channel 208, and is illustrated as laterally outwardly spaced from the channel 208 with respect to the previously implanted rod 24. The channels 208 extend longitudinally, in a direction substantially parallel to the previously implanted fixation rod 24, though it should be appreciated that the linkage 247, and thus the channel 212, can alternatively be angularly offset with respect to the fixation rod 24.

Figure 14A:
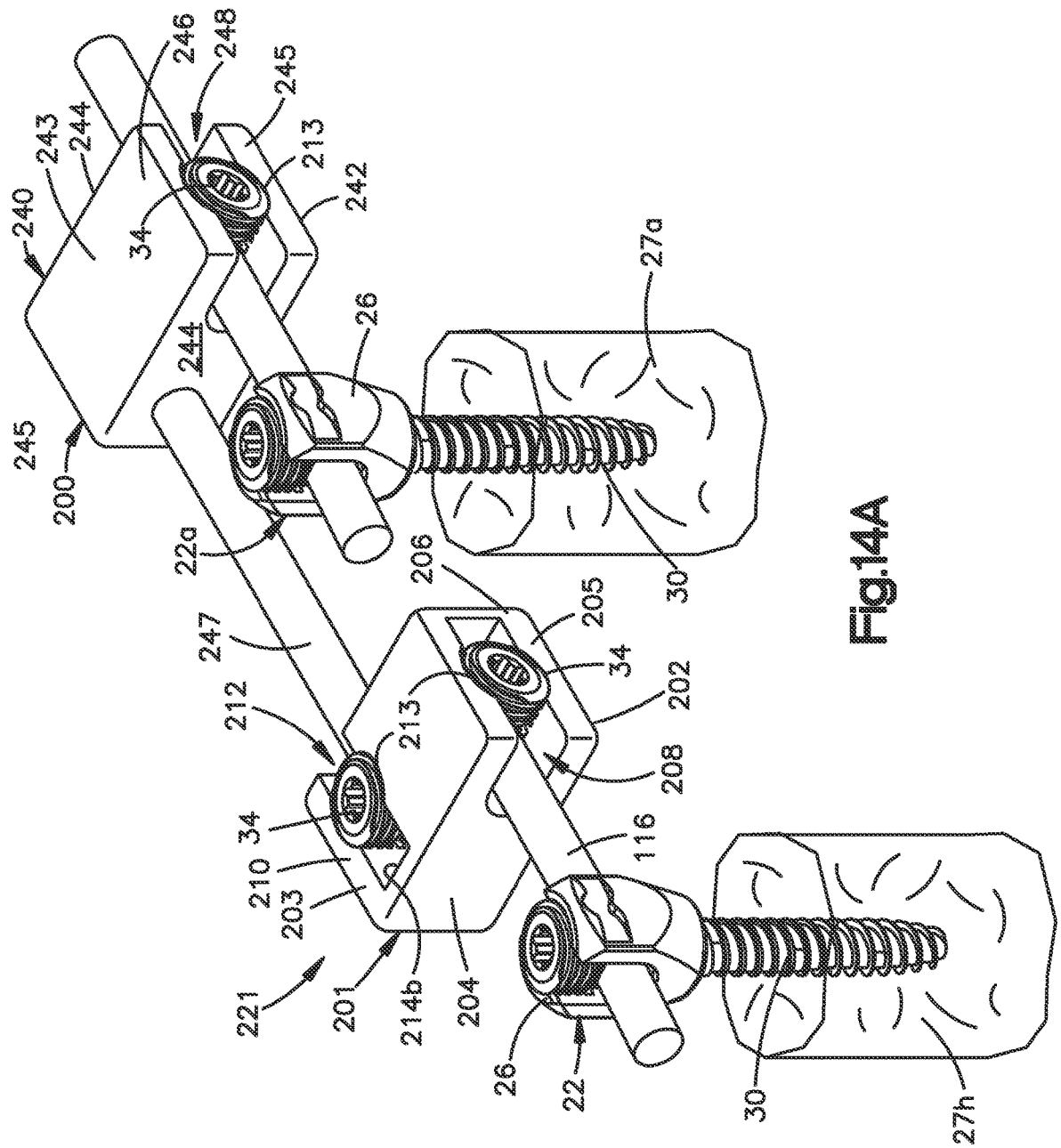
FIG. 14A is a perspective view of a revision connector constructed in accordance with another alternative embodiment, including a first connector body and a second connector body.

As illustrated in FIG. 14A, the first rod receiving channel 208 extends laterally into the side surface 245, though the first rod receiving channel 208 can alternatively extend vertically into the outer surface 243 of the first connector body 201 as shown in FIGS. 14B-C. Furthermore, while the second rod receiving channel 212 extends vertically into the outer surface 243 of the first connector body 201 as illustrated in FIG. 14A, the second rod receiving channel 212 could alternatively extend laterally into the side surface 245 as illustrated in FIG. 14B. As shown in FIGS. 14B-C, the rod receiving channels 208 and 212 can be laterally adjacent and aligned with each other. The channels 208 and 212 could alternatively be vertically or longitudinally aligned with each other, if desired.

With continuing reference to FIG. 14A, the second body 240 defines an inner vertebral facing surface 242, an opposing outer surface 243 separated from the inner surface 242 along the axial direction A, opposing end surfaces 244 connected between the inner and outer surfaces 242 and 243 and spaced apart in the longitudinal direction L, and opposing side surfaces 245 connected between the inner and outer surfaces 242 and 243, further connected between the end surfaces 244, and spaced apart in the lateral direction. It should be appreciated that, depending on the orientation of the second connector body 240, one of the end surfaces 244 can be positioned as a superior end surface, while the other end surface 244 can be positioned as an inferior end surface once the connector 200 has been implanted. While the connector 200 is illustrated having a generally rectangular structure having the discrete surfaces 242-245, it should be appreciated that any shaped structure can define the surfaces as described herein as desired, even though the surfaces may be curved or angled with respect to the longitudinal, axial, and/or lateral directions.

The second connector body 240 defines a head 246 and a rod receiving channel 248 that extends longitudinally through the head 246 between the opposing end surfaces 244. The rod receiving channel 248 further extends laterally into the side surface 245 located proximate to the previously implanted fixation rod 24. The rod receiving channel 248 is thus configured to receive the previously implanted fixation rod 24. A pair of threaded opposing arcuate cutouts 213 extends into each connector body 201 and 204 at locations aligned with the rod receiving channels 208, 212, and 248, and is configured to receive the locking cap in the manner described above with respect to the connector body 101.

The second body 240 also defines a linkage 247 that extends from the inner end surface 244, that is the end surface 244 that faces toward the first body, in a direction toward the first body 201. As illustrated, the linkage 247 is laterally offset, and displaced laterally outward, with respect to the channel 248, and thus the previously implanted spinal fixation rod 24. Thus, the first body 240 extends in a direction angularly offset, and substantially perpendicular, with respect to the previously implanted fixation rod 24. The linkage 247 can be provided as cylindrical or tubular, and thus constructed in the same manner as the fixation rods 24 and 116. The linkage 247 can be integrally connected or discretely attached to the second body 240. For instance, the second body 240 can include a head having a rod receiving channel that receives and secures the linkage 247 to the second body in the manner described herein with respect to the channel 212.

Figure 15C:
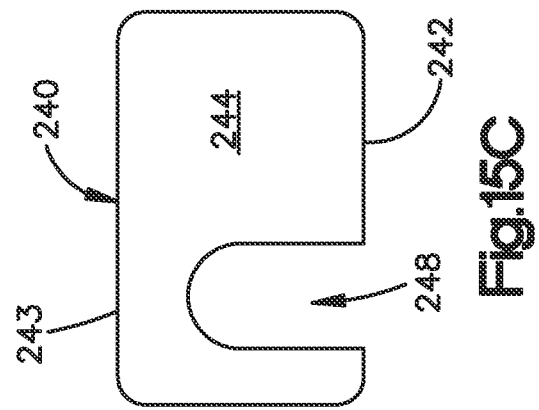
FIG. 15C is a schematic elevation view similar to FIG. 15B, but showing the second connector body constructed in accordance with another alternative embodiment.
Figure 15B:
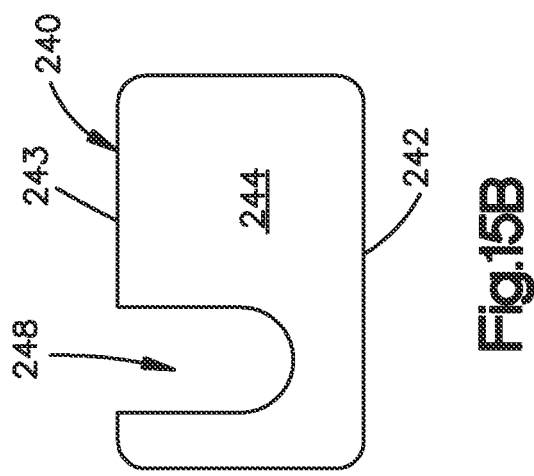
FIG. 15B is a schematic elevation view similar to FIG. 15A, but showing the second connector body constructed in accordance with an alternative embodiment.
Figure 15A:
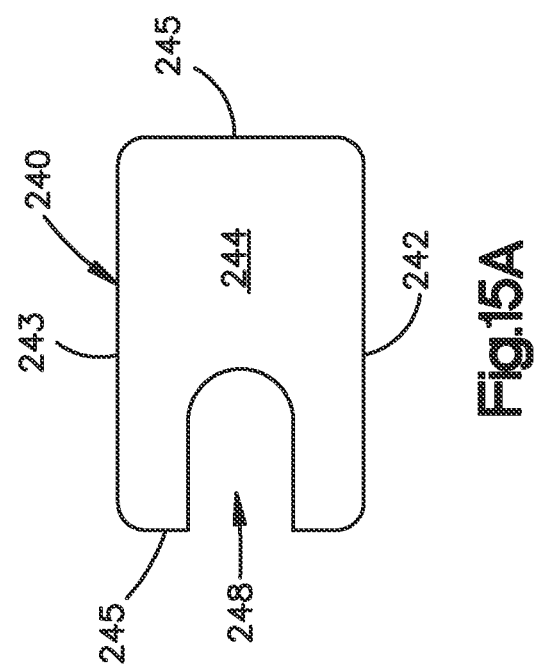
FIG. 15A is a schematic end elevation view of the second connector body illustrated in FIG. 14A.
Figure 17A:
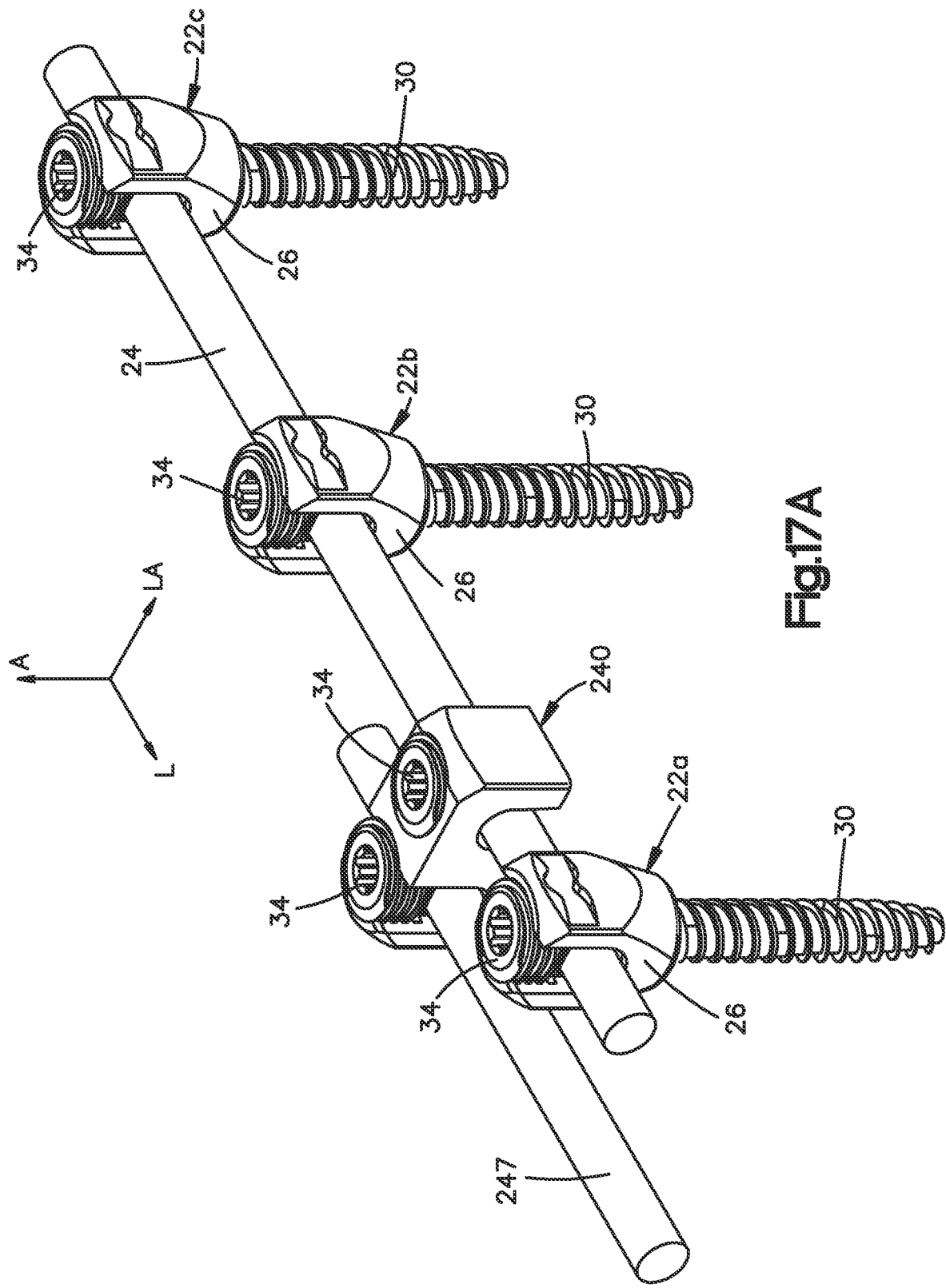
FIG. 17A is a perspective view of the second revision connector body illustrated in FIG. 14A constructed in accordance with an alternative embodiment.
Figure 18:
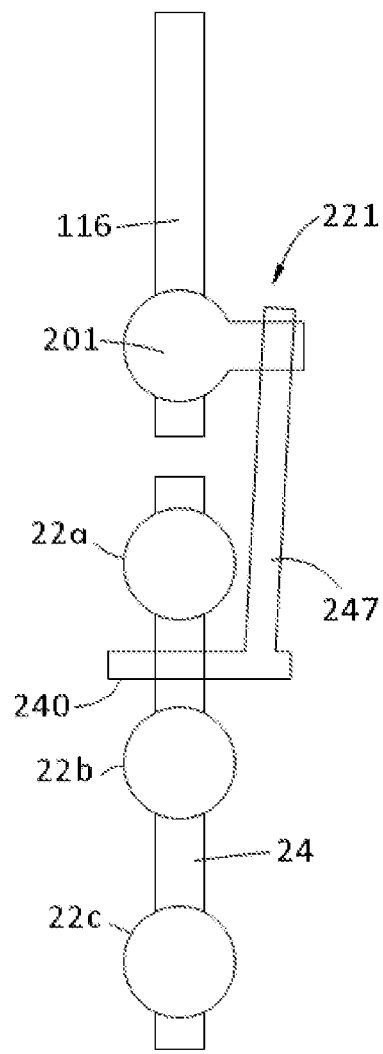
FIG. 18 is a schematic view illustrating a revision connector system similar to that illustrated in FIG. 14A with a linkage that is angularly offset with respect to a previously implanted fixation rod.

As illustrated in FIGS. 14A and 15A, the rod receiving channel 248 can alternatively extend laterally into the side wall 245 that is disposed proximate to the previously implanted rod 24. However, it should be appreciated that the rod receiving channel 248 can alternatively extend vertically into the outer surface 243 or the inner surface 242 as illustrated in FIGS. 15B and 15C, respectively. It should be appreciated that any of the rod receiving channels described herein in accordance with all embodiments could alternatively extend longitudinally into the respective end surfaces without also extending into one of the inner, outer, and side surfaces, unless otherwise indicated. In this embodiment, the fixation rod would be inserted longitudinally into the respective head of the connector body.

Referring now also to FIGS. 14A and 16A-D, a method for extending the pre-existing bone fixation assembly 20 can be provided without cutting the previously implanted spine fixation rod 24 or removing the outermost bone fixation element 22. During operation, the first connector body 201 is fixed via one or more bone anchors 30 to at least one such as a plurality of vertebrae (e.g., the pedicle of the vertebrae) that are superior and/or inferior to the previously fixed vertebrae. The first connector body 201 can be secured to vertebrae 27g-h to extend the bone fixation assembly 20 craniallly, and to vertebrae 27e-f to extend the bone fixation assembly caudally.

The second connector body 240 is then urged onto the previously implanted fixation rod 24 at a location between a pair of the previously implanted bone fixation elements 22, so that the rod 24 is disposed in the rod receiving channel 248. For instance, when extending the bone fixation assembly cranially, the channel 248 can receive the rod 24 at a location between inferior to the superior vertebra 271, such as between the superior vertebra 27a and the adjacent vertebra 27b. When extending the bone fixation assembly caudally, the channel 248 can receive the rod 24 at a location superior to the inferior vertebra 27d, such as between the inferior vertebra 27d and the adjacent vertebra 27c.

The second connector body 240 thus extends from the previously implanted spine fixation rod 24 laterally outward such that the linkage 247 is laterally offset from the rod 24 and extends substantially parallel to the rod 24. The first connector body 201 is then urged to the linkage 247 so as to receive the linkage 247 in the rod receiving channel 212. The linkage 247 can be laterally or vertically inserted into the channel 212. The first connector body 201 is then urged to the new spine fixation rod 116, such that the rod 116 is received in the first rod receiving channel 208, thereby coupling the bone anchor 30 that is extending from the connector 201 to the second connector body 240. The connector body 201 can be secured to the fixation rod 116 and the linkage 247, and the second connector body 240 can be secured to the fixation rod 24, by tightening respective locking caps in the channels in the manner described above. Alternatively, for instance when extended the bone fixation assembly 20 only one level, a locking plug can be inserted into the channel 208. The locking plug can be constructed similar to the locking screws known in the art with the exception that a rod segment is attached thereto and fixed to the underlying vertebrae in the manner described above.

As described above, the second connector body 240 can be discretely connected to the linkage 247. For instance, referring to FIGS. 17A-D, the connector body 240 includes a head 251 laterally adjacent to the head 246, and a rod receiving channel 250 extending vertically down into the outer surface 243, and extending longitudinally through the head 251. The channel 250 extends longitudinally into the inner end surface 244, and can extend longitudinally through the connector body 240 and through the opposing outer end surface 244. An arcuate cutout 213 can extend vertically into the connector body 240 in a direction transverse to and in alignment with the channel 250 so as to receive a locking cap 34 of the type described above. The linkage 247 can be provided as a rod segment that is received in the channel 250, such that the locking cap 34 can be tightened against the linkage 247 to secure the linkage 247 in the channel 250. It should be appreciated that the channel 250 can alternatively extend into the inner surface 242, or the outer side surface 245 as desired.

The channel 248 is illustrated as extending up into the inner surface 242 of the connector body 240 at a location laterally offset and aligned with the channel 250. Accordingly, the connector body 240 defines an S-shape as illustrated in end elevation. Alternatively, the channel 248 can extend into any surface of the connector body 240 as desired. The channel 248 extends in the longitudinal direction L through the connector body 240, and is thus configured to receive the previously implanted rod 24 extending along the longitudinal direction. The connector body 240 can define a bore 249 extending vertically down from the outer surface 243 into the channel 248.

The revision connector system 221 can include a clamp 252 having a clamp body 253 that has an outer diameter substantially equal to the inner diameter of the bore 249. The clamp body 253 can include an horizontal support wall 254 and a pair of legs 256 extending down from the upper support wall 254. The upper support wall 254 can include a threaded surface 255 configured to engage corresponding external threads 257 of the locking cap 34 inside the bore 249. Thus, as the locking cap 34 is rotated in a first direction, the clamp 252 is moved upwards in the bore, thereby causing the legs 256 to compress toward each other. Thus, the legs 256 are flexible and sized to fit over the previously implanted rod 24 when the legs 256 extend down past the connector body 240. The legs 256 and upper support wall 254 thus define a channel 258 that is disposed in the channel 248 defined by the connector body. Once the previously implanted rod 24 is inserted into the channel 258, the locking cap 34 is tightened so as to cause the connector body 240 to bias the legs 256 toward each other so as to fit around the previously implanted rod 24 and secure the rod 24 to the connector body 240. The linkage 247 can be fixed onto one or more cranial or caudal vertebrae via one or more pedicle screw assemblies 75, or can be secured to the connector body 201 as described above.

It should be appreciated that a plurality of revision connector embodiments has been described herein. Thus a spine fixation revision connector kit can be provided that includes a plurality of revision connectors, each revision connector being configured to couple a new spine fixation rod to a previously implanted spine fixation rod that is secured to a plurality of vertebrae. Each revision connector in the kit can include a first head and a first rod receiving channel extending into the first head, and a second head and a second rod receiving channel extending into the second head. At least one different revision connector of the plurality of revision connectors defines a difference with respect to at least another of the plurality of revision connectors in the kit. For instance, the different revision connector comprises an opening extending into at least a select one of the first and second heads along a direction transverse to the corresponding rod receiving channel. The difference can also be in the form of a shape of the connector body. For instance, the difference can be that the connector body defines an anchor seat body. The difference can also be the location of the rod receiving channel. The kit can also be a revision connector system kit that includes a plurality of linkages 247 and/or new fixation rods 116 alone or in combination with the spine fixation revision connector kit.

It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention as defined by the present description.

We claim:

1. A method of coupling a first spine fixation rod to at least one vertebra and a second spine fixation rod, the method comprising:
receiving the first spine fixation rod in a rod receiving channel, defined by a body of a first connector, such that the first spine fixation rod extends from the body of the first connector along a first direction;

positionally locking the first spine fixation rod in the rod receiving channel such that the first spine fixation rod extends from the body along the first direction;

receiving a rod of the first connector in a channel of a second connector, wherein the rod extends integrally out from the body such that the body and rod together define a one-piece structure; and coupling the rod of the first connector, via the second connector, to the second spine fixation rod, which is coupled to at least one vertebra that is different than the at least one vertebra to which the first spine fixation rod is coupled, wherein the first connector is not directly connected to any underlying vertebra via any bone anchor that extends through the first connector.

2. The method of claim 1, wherein the rod of the first connector extends out from the body along a second direction that is angularly offset with respect to the first direction so as to be non-parallel with the first direction when the first spine fixation rod is disposed in the rod receiving channel.

3. The method of claim 2, wherein the second direction is angularly offset with respect to the first direction as viewed in a plane that is perpendicular to a vertical direction that is perpendicular to the first direction.

4. The method of claim 2, wherein the rod extends along the second direction as it extends out from the body.

5. The method of claim 1, wherein the body includes a head having an inner vertebral facing surface and an opposed outer surface spaced from one another along a vertical direction that is perpendicular to the first direction, and wherein the rod receiving channel extends through the head along the first direction and is open at the outer surface along an entire length of the rod receiving channel along the first direction.

6. The method of claim 1, wherein the rod receiving channel receives the first spine fixation rod along a vertical direction that is perpendicular to the first direction and wherein the second connector is not directly connected to any underlying vertebra via any bone anchor that extends through the second connector, and wherein both of the at least one vertebra and the at least one vertebra that is different than the at least one vertebra are offset from the rod receiving channel along the first direction.

7. The method of claim 1, wherein the body includes a head that defines a threaded internal surface that receives a locking cap along a vertical direction, that is perpendicular to the first direction, so as to secure the first spine fixation rod when the first spine fixation rod is received in the rod receiving channel.

8. The method of claim 1, wherein the body has first and second end surfaces spaced from one another along the first direction, and the rod receiving channel defines a first opening at the first end surface and a second opening at the second end surface.

9. The method of claim 8, wherein each of the first and second openings extends from an outer surface, of the body, towards an inner vertebral facing surface, of the body, such that the first and second openings are open at the outer surface.

10. A method of coupling a first spine fixation rod to a second spine fixation rod, the method comprising:

receiving a linkage rod in a linkage rod-receiving channel of a first body that defines a first head;

coupling the first head to a second head, with the linkage rod, such that the first head is rotatable about an axis of the linkage rod; and retaining the first spine fixation rod, in a first fixation rod channel that extends along a longitudinal direction and is defined by the first head, and retaining the second spine fixation rod, in a second fixation rod channel defined by the second head, when the linkage rod couples the first head to the second head, thereby coupling the first spine fixation rod to the second spine fixation rod such that the first and second spine fixation rods extend from the first and second fixation rod channels, respectively, in the longitudinal direction and the linkage rod is elongate in a direction that is angularly offset with respect to the longitudinal direction so as to be non-parallel with the longitudinal direction, wherein the first body is not directly connected to any underlying vertebra via any bone anchor that extends through the first body.

11. The method of claim 10, wherein the first fixation rod channel extends into an outer surface of the first head towards an inner vertebral facing surface of the first head along a vertical direction, perpendicular to the longitudinal direction, such that the first fixation rod channel is open at the outer surface of the first head along an entire length of the first fixation rod channel along the longitudinal direction.

12. The method of claim 10, wherein the first and second fixation rod channels are oriented such that the first and second spine fixation rods extend from the first and second fixation rod channels, respectively, in the longitudinal direction and the linkage rod is elongate in a direction that is angularly offset with respect to the longitudinal direction so as to be non-parallel with the longitudinal direction.

13. The method of claim 10, wherein the second fixation rod channel extends through the second head along the longitudinal direction and extends into an outer surface of the second head towards an inner vertebral facing surface of the second head along a vertical direction such that the second fixation rod channel is open at the outer surface of the second head along an entire length of the second fixation rod channel along the longitudinal direction.

14. The method of claim 10, wherein the first fixation rod channel receives the first spine fixation rod along a vertical direction that is perpendicular to the longitudinal direction.

15. The method of claim 10, wherein the second fixation rod channel receives the second spine fixation rod along a vertical direction that is perpendicular to the longitudinal direction.

16. The method of claim 10, wherein the first head defines a threaded internal surface that receives a locking cap along a vertical direction, that is perpendicular to the longitudinal direction, so as to secure the first spine fixation rod when the first spine fixation rod is received in the first fixation rod channel.

17. The method of claim 10, wherein the first head has first and second end surfaces spaced from one another along the longitudinal direction, and the first fixation rod channel defines a first opening at the first end surface and a second opening at the second end surface.

18. The method of claim 17, wherein each of the first and second openings extends from an outer surface of the first head towards an inner vertebral facing surface of the first head such that the first and second openings are open at the outer surface.

19. The method of claim 10, wherein the second head defines a threaded internal surface that receives a locking cap along a vertical direction so as to secure the second spine fixation rod when the second spine fixation rod is received in the second fixation rod channel.

20. The method of claim 10, wherein the second head has a first end surface and a second end surface that are spaced from one another along the longitudinal direction, and the second fixation rod channel defines a first opening at the first end surface of the second head and a second opening at the second end surface of the second head.

* * * * *